(12) United States Patent
Massari et al.

(10) Patent No.: US 7,368,541 B2
(45) Date of Patent: May 6, 2008

(54) TRACE AMINE RECEPTOR 1 OF THE AFRICAN GREEN MONKEY

(75) Inventors: Mark Eben Massari, San Diego, CA (US); Herve Schaffhauser, Harleysville, PA (US); Satoshi Ozaki, Ibaraki (JP)

(73) Assignee: Merck & Co., Inc., Rahway, NJ (US)

( * ) Notice: Subject to any disclaimer, the term of this patent is extended or adjusted under 35 U.S.C. 154(b) by 76 days.

(21) Appl. No.: 11/291,686

(22) Filed: Dec. 1, 2005

(65) Prior Publication Data

US 2006/0115858 A1      Jun. 1, 2006

Related U.S. Application Data

(60) Provisional application No. 60/632,142, filed on Dec. 1, 2004.

(51) Int. Cl.
*C07K 14/705*   (2006.01)
*C12N 15/12*   (2006.01)

(52) U.S. Cl. ............... 530/350; 435/69.1; 536/23.5

(58) Field of Classification Search ............... None
See application file for complete search history.

(56) References Cited

U.S. PATENT DOCUMENTS 6,783,973 B1   8/2004   Bunzow et al.

FOREIGN PATENT DOCUMENTS

| WO | WO 00/73449 | 12/2000 |
|----|-------------|---------|
| WO | WO 01/72841 | 10/2001 |
| WO | WO 02/22801 A3 | 3/2002 |

OTHER PUBLICATIONS

Borowsky, et al., "Trace amines: Identification of a family of mammalian G protein-coupled receptors", PNAS, Jun. 31, 2001, vol. 98, No. 16, pp. 8966-8971.
Branchek, et al., "Trace amine receptors as targets for novel therapeutics: legend, myth and fact", Current Opinion in Pharmacology, vol. 3, pp. 90-97, 2003.
Bunzow, et al., "Amphetamine, 3,4-Methylenedioxymethamphetamine, Lysergic Acid Diethylamide, and Metabolites of the Catecholamine Neurotransmitters Are Agonists of a Rat Trace Amine Receptor," Molecular Pharmacology, vol. 60, No. 6, pp. 1181-1188, 2001.
D'Andrea, et al., Elevated levels of circulating trace amines in primary headaches, Neurology, vol. 62, May 2004, pp. 1701-1705.
GenBank AY135366, May 18, 2005.
GenBank NM_053205, Apr. 16, 2005.
GenBank NM_134328, Oct. 17, 2005.
GenBank NM_138327, Oct. 21, 2005.
Kim, et al., "Old Drugs Learn New Tricks: Insights from Mammalian Trace Amine Receptors", Molecular Pharmacology, vol. 60, No. 6, p. 1165-1167, 2001.
Miller, et al., "Cloning of Rhesus Monkey TAR-1, A Novel G-Protein-Linked Receptor for "Trace" Amines", Program 10.1, 2002 Abstract Viewer/Itinerary Planner, Washington, DC: Society for Neuroscience, 2002.

*Primary Examiner*—John Ulm
(74) *Attorney, Agent, or Firm*—Joan E. Switzer; William Krovatin

(57) ABSTRACT

A trace amine receptor 1 has been isolated from the genome of *Cercopithecus aethiops* (African green monkey). Described is the amino acid sequence of the receptor, the nucleic acid encoding the receptor, and methods for using the receptor to identify analytes that are agonists or antagonists of the receptor.

1 Claim, 4 Drawing Sheets

FIGURE 1

```
ATGCCCTTTT GCCACAATAT AATTAATACT TCCTGTGTGA AAAACAACTG GTCAAATGAT    60
GTCCGTGCTT CCCTGTACAG TTTAATGGCG CTCATAATTC TGACCACATT GGTCGGCAAT   120
CTGATAGTTA TTGTTTCTAT ATCACACTTC AAGCAACTTC ATACTCCGAC AAATTGGCTC   180
ATTCATTCCA TGGCCACTGT GGACTTTCTT CTGGGGTGTC TGGTCATGCC TTACAGCATG   240
GTGAGATCTG CTGAGCACTG TTGGTATTTT GGAGAAGTCT TCTGTAAAAT CCACACCAGC   300
ACCGACATTA TGCTGAGCTC AGCCTCCATT TTCCATCTGT CTTTCATCTC CATTGACCGC   360
TACTATGCTG TGTGTGACCC ATTGAGATAT AAAGCCAAGA TCAATATCTT GGTTATTTGT   420
GTGATGATCT TCATTAGTTG GAGTGTCCCT GCTGTTTTTG CATTTGGGAT GATCTTTCTG   480
GAGCTAAACT TCAAAGGCGC TGAAGAGATA TATTACAAAC ATGTTCACTG CAGAGGAGGT   540
TGCTCTGTGT TCTTTAGCAA TCTTTAGCAA GTACTGGCCT TTATGACTTC TTTTACATA    600
CCTGGATCTA TTATGTTATG TATCTATTAC AGAATATATC TTATAGCTAA AGAGCAGGCA   660
AGATCAATTA ATGATGCCAA TCAGAAGCTC CAAATTGGGA TGGAAATGAA AAATGGAATT   720
TCACAAAGCA AGAGAAAGGAA AGCTGCGAAG ACATTGGGGA TTGTGATGGG AGTTTCCTA   780
ATATGCTGGT GCCCTTTCTT TGTCTGTACA GTCATCGACC CTTTTCTTCA CTACACTCTT   840
CCACCTACTT TGAATGATGT ATTGATTTGG TTTGGCTACT TGAACTCGAC ATTAATCCA    900
ATGGTTTATG CATTTTTCTA TCCCTGGTTT AGAAAAGCAC TGAAGATGAT TCTGTTTGGT   960
AAAATTTTCC AAAAAGATTC ATCCAGGTGT AATTATTTT TGGAATCGAG TTCATAG      1017
```

```
MPFCHNIINT  SCVKNNWSND  VRASLYSLMA  LIILTTLVGN  LIVIVSISHF  KQLHTPTNWL   60
IHSMATVDFL  LGCLVMPYSM  VRSAEHCWYF  GEVFCKIHTS  TDIMLSSASI  FHLSFISIDR  120
YYAVCDPLRY  KAKINILVIC  VMIFISWSVP  AVFAFGMIFL  ELNFKGAEEI  YYKHVHCRGG  180
CSVFFSKISG  VLAFMTSFYI  PGSIMLCIYY  RIYLIAKEQA  RSINDANQKL  QIGLEMKNGI  240
SQSKERKAAK  TLGIVMGVFL  ICWCPFFVCT  VIDPFLHYTL  PPTLNDVLIW  FGYLNSTFNP  300
MVYAFFYPWF  RKALKMILFG  KIFQKDSSRC  KLFLESSS                            338
```

FIGURE 2

```
African Green Monkey TA1 receptor   (1)   -MPFCHNIINTSCVKNNWSNDVRASLYSLMALIILTTLVGNLIVIVSISH
             Rhesus TA1 receptor    (1)   -MPFCHNIINISCVKNNWSNDVRASLYSLMALIILTTLVGNLIVIVSISH
                Rat TA1 receptor    (1)   -MHLCHNSANISHTNSNWSRDVRASLYSLISLIILTTLVGNLIVIISISH
              Human TA1 receptor    (1)   MMPFCHNIINISCVKNNWSNDVRASLYSLMVLIILTTLVGNLIVIVSISH
                                    51                                                    100
African Green Monkey TA1 receptor  (50)   FKQLHTPTNWLIHSMATVDFLLGCLVMPYSMVRSAEHCWYFGEVFCKIHT
             Rhesus TA1 receptor   (50)   FKQLHTPTNWLIHSMATVDFLLGCLVMPYSMVRSAEHCWYFGEVFCKIHT
                Rat TA1 receptor   (50)   FKQLHTPTNWLLHSMAVVDFLLGCLVMPYSMVRTVEHCWYFGELFCKLHT
              Human TA1 receptor   (51)   FKQLHTPTNWLIHSMATVDFLLGCLVMPYSMVRSAEHCWYFGEVFCKIHT
                                   101                                                   150
African Green Monkey TA1 receptor (100)   STDIMLSSASIFHLSFISIDRYYAVCDPLRYKAKINILVICVMIFISWSV
             Rhesus TA1 receptor  (100)   STDIMLSSASIFHLSFISIDRYYAVCDPLRYKAKINILVVCVMIFISWSV
                Rat TA1 receptor  (100)   STDIMLSSASILHLAFISIDRYYAVCDPLRYKAKINLAAIFVMILISWSL
              Human TA1 receptor  (101)   STDIMLSSASIFHLSFISIDRYYAVCDPLRYKAKMNILVICVMIFISWSV
                                   151                                                   200
African Green Monkey TA1 receptor (150)   PAVFAFGMIFLELNFKGAEEIYKHVHCRGGCSVFFSKISGVLAFMTSFY
             Rhesus TA1 receptor  (150)   PAVFAFGMIFLELNFKGAEEIYKHVHCRGGCSVFFSKISGVLAFMTSFY
                Rat TA1 receptor  (150)   PAVFAFGMIFLELNLEGVEELYHNQVFCLRGCFPFFSKVSGVLAFMTSFY
              Human TA1 receptor  (151)   PAVFAFGMIFLELNFKGAEEIYKHVHCRGGCSVFFSKISGVLTFMTSFY
                                   201                                                   250
African Green Monkey TA1 receptor (200)   IPGSIMLCIYYRIYLIAKEQARSINDANQKLQIGLEMKNGISQSKERKAA
             Rhesus TA1 receptor  (200)   IPGSIMLCIYYRIYLIAKEQARSINDANQKLQIGLEMKNGISQSKERKAV
                Rat TA1 receptor  (200)   IPGSVMLFVYYRIYFIAKGQARSINRAN--LQVGLEGESRAPQSKETKAA
              Human TA1 receptor  (201)   IPGSIMLCVYYRIYRIYLIAKEQARLISDANQKLQIGLEMKNGISQSKERKAV
                                   251                                                   300
African Green Monkey TA1 receptor (250)   KTLGIVMGVFLICWCPFFVCTVIDPFLHYTLPPTLNDVLIWFGYLNSTFN
             Rhesus TA1 receptor  (250)   KTLGIVMGVFLICWCPFFVCTVIDPFLHYTIPPTLNDVLIWFGYLNSTFN
                Rat TA1 receptor  (248)   KTLGIMGVFLLCWCPFFFCMVLDPFLGYVIPPTLNDTLNWFGYLNSAFN
              Human TA1 receptor  (251)   KTLGIVMGVFLICWCPFFICTVMDPFLHYIIPPTLNDVLIWFGYLNSTEN
                                   301                                                   339
African Green Monkey TA1 receptor (300)   PMVYAFFYPWFRKALKMILFGKIFQKDSSRCKLFLESSS-
             Rhesus TA1 receptor  (300)   PMVYAFFYPWFRKALKMILFGKIFQKDSSRCKLFLESSS-
                Rat TA1 receptor  (298)   PMVYAFFYPWFRRALKMVLFGKIFQKDSSRSKLFL-----
              Human TA1 receptor  (301)   PMVYAFFYPWFRKALKMMLFGKIFQKDSSRCKLFLELSS-
```

TRACE AMINE RECEPTOR 1 OF THE AFRICAN GREEN MONKEY

CROSS REFERENCE TO RELATED APPLICATIONS

This application claims benefit of U.S. Provisional Applications No. 60/632,142 filed Dec. 1, 2004.

BACKGROUND OF THE INVENTION (1) Field of the Invention

The present invention relates to the *Cercopithecus aethiops* (African green monkey) trace amine receptor 1, the nucleic acid encoding the receptor, and methods for identifying analytes that are agonists or antagonists of the receptor.

(2) Description of Related Art

Norepinephrine, dopamine, and serotonin are biogenic amine neurotransmitters that exert their effects through interactions with subfamilies of receptors that belong to the rhodopsin superfamily of G protein-coupled receptors (GPCRs). In addition to these biogenic amine neurotransmitters, there exists a class endogenous amines ("trace amines") that are found in very low levels in the tissues of a wide variety of organisms, including humans. These trace amines, which include tyramine, β-phenylethylamine (β-PEA), tryptamine, and octopamine and which are chemically related to the biogenic amines, are produced both in the body and obtained from the diet from foods such as chocolate, aged cheese, beer, soy sauce, and wine.

Trace amines exert various pharmacological effects. For example, the role of trace amines as neurotransmitters in invertebrates has been well established and octopamine is thought to be the sympathetic nervous system counterpart to norepinephrine. While the role of trace amines as neurotransmitters in mammalian systems has not been thoroughly examined, trace amines have been found to affect the uptake or release of catcholamines, or 5-HT activity, at nerve endings. Because a number of drugs that stimulate trace amine receptors alter a person's perception of reality, trace amine receptors may have an important role in the brain's response or processing of sensory information. Thus, disruptions or alterations in the trace amine system may be involved in depression as well as other psychiatric and neurological disorders, including migraines and headaches (See Branchek and Blackburn, Curr. Opin. Pharmacol. 3: 90-97 (2003); Kim and Zastrow, Mol. Pharmacol. 60: 1165-1167 (2001)). For example, D'Andrea et al. (Neurol. 62: 1701-1705 (2004)) have found elevated levels of trace amines in the plasma of patients with cluster headaches and migraines. Their results suggest that receptors for trace amines may be involved in the etiology of migraines and headaches.

Mammalian trace amine receptors 1 have been cloned from the mouse (Borowsky et al., Proc. Natl. Acad. Sci. U.S.A. 98 (16), 8966-8971 (2001); GenBank NM_053205), rat (Bunzlow et al., Molec. Pharmacol. 60: 1181-1188 (2001); GenBank NM_134328), rhesus monkey (Miller and Madras, Neurosci Abstr. 10: 1 (2002); GenBank AY135366), and human (Bunzlow et al., ibid.; GenBank NM_138327). Trace amine receptors has been reviewed by Brancheck and Blackburn, Curr. Opin. Pharmacol. 3: 90-97(2003) and have been disclosed in WO 0172841, WO 0222801 and U.S. Pat. No. 6,783,973 to Bunzow and Grady, and WO 00734499 to Ogozalek et al.

The trace amine receptor 1 is a transmembrane protein comprising the classical GPCR structure: an extracellular or ligand binding domain, seven transmembrane domains, and a cytoplasmic domain which interacts with Gα of the set of heterotrimeric G proteins. In the inactive state, Gα is bound to GDP. When a trace amine binds to the ligand binding domain, a signal is transduced through the receptor which results in the GDP bound to Gα to be replaced by GTP and the Gα to dissociate from Gβ and Gγ (which remain as a GβGγ dimer). Gα and the GβGγ dimer activate effectors, which in turn, activate distinct intracellular pathways specific to the receptor and G protein. At present, more than five different Gα proteins subtypes are known; e.g., $G_s$, $G_{i/o}$, $G_q$, $G_{12}$, and $G_{13}$. $G_s$ activates adenyl cyclase, $G_{i/o}$ inhibits adenyl cyclase, and $G_q$ activates phospholipase C beta (PLC) which cleaves phosphoinositol-4,5 bisphosphate ($PIP_2$) in the cell membrane to release second messengers diacylglycerol (DAG) and inositol-(1,4,5)-triphosphate ($IP_3$). $G_{12}$ and $G_{13}$ interact with Rho-specific guanine nucleotide exchange factors and regulate the actin cytoskeleton; however, $G_{12}$ and $G_{13}$ do not appear to have an important role in the function of GPCRs. Because stimulation of the human trace amine receptor 1 by various agonists produces an increase in cAMP accumulation, it is likely that the trace amine receptor 1 signals through a $G_s$-mediated signal transduction pathway (Borowsky et al., Proc. Natl. Acad. Sci. 98: 8966-8971 (2001)).

Because trace amines appear to be neurotransmitters with a role in various human psychiatric and neurological disorders, there is a need for methods for identifying agonists and antagonists of trace amine receptor 1 that can be used in therapies to treat the above disorders.

BRIEF SUMMARY OF THE INVENTION

The present invention provides the *Cercopithecus aethiops* (African green monkey) traceh amine receptor 1 (agmTA1 receptor), the nucleic acid encoding the receptor, and methods for identifying analytes that are agonists or antagonists of the receptor. Analytes identified using the present invention may be useful for treating a variety of psychiatric and neurological diseases and disorders.

Therefore, the present invention provides an isolated nucleic acid molecule comprising a nucleotide sequence encoding an agmTA1 receptor or fragment thereof, preferably an agmTA1 receptor or fragment thereof, which comprises an amino acid sequence of SEQ ID NO:2. In various embodiments, the isolated nucleic acid is a DNA, an RNA, or a cDNA. In a further embodiment of the nucleic acid, the nucleotide sequence of the nucleic acid comprises a nucleotide sequence of SEQ ID NO:1.

The present invention further provides an isolated protein or fragment thereof comprising the amino acid sequence or part thereof of SEQ ID NO:2.

The present invention further provides an antibody that binds a protein comprising the amino acid sequence or part thereof of SEQ ID NO:2. In particular embodiments, the antibody is selected from the group consisting of polyclonal antibodies, monoclonal antibodies, recombinant scFv polypeptides, recombinant $V_H$ polypeptides, and variants thereof.

The present invention further provides a vector comprising a nucleic acid encoding an agmTA1 receptor or fragment thereof. Preferably, the agmTA1 receptor or fragment thereof comprises an amino acid sequence of SEQ ID NO:2.

The present invention further provides a gene expression cassette comprising a nucleic acid encoding an agmTA1 receptor or fragment thereof. Preferably, the agmTA1 receptor or fragment thereof comprises an amino acid sequence of SEQ ID NO:2. In further embodiments of the gene expression cassette, the nucleic acid encoding the agmTA1 receptor is operably linked to a heterologous promoter that can either be constitutive or inducible. In a further aspect, the present invention provides an expression cassette comprising a transcriptional initiation region functional in a host cell, a nucleic acid comprising the nucleic acid sequence of SEQ ID NO:1 operably linked to the transcriptional initiation region, and a transcriptional termination region functional in the host cell.

The present invention further provides a cell comprising a nucleic acid encoding an agmTA1 receptor or fragment thereof which preferably comprises an amino acid sequence as set forth of SEQ ID NO:2 wherein the nucleic acid is operably linked to a heterologous promoter which can either be constitutive or inducible. In a further embodiment of the cell, the nucleic acid is integrated into the genome of the cell. In a further aspect, the present invention provides a recombinant cell comprising an expression cassette as disclosed herein as part of an extrachromosomal element or integrated into the genome of a host cell as a result of introduction of the expression cassette into the host cell.

The present invention further provides a method for producing an agmTA1 receptor comprising providing a nucleic acid encoding the agmTA1 receptor operably linked to a heterologous promoter; introducing the nucleic acid into a cell to produce a recombinant cell; and culturing the recombinant cell under conditions which allows expression of the agmTA1 receptor encoded by the nucleic acid to produce the agmTA1 receptor. In a further aspect, the present invention provides a method of producing an agmTA1 receptor in vitro, the method comprising culturing a recombinant cell as disclosed herein, whereby the agmTA1 receptor is expressed and isolating the agmTA1 receptor. In further embodiments, the nucleic acid is integrated into the genome of the recombinant cell. In a further still embodiment of the method, the agmTA1 receptor comprises the amino acid sequence of SEQ ID NO:2.

The present invention is particularly useful for identifying analytes useful for treating or preventing diseases associated with TA1 receptor activity. Therefore, the present invention further provides a method for screening for analytes useful for treating or preventing diseases associated with TA1 receptor activity in a mammal, which comprises in one aspect determining the activity of an agmTA1 receptor in the presence of a particular concentration of the analyte or in the absence of the analyte, and determining the activity of the agmTA1 receptor at a different concentration of the analyte. The screening method can be cell-based or cell-free and can comprise one or more embodiments of the functional or binding assays set forth below.

Functional assays include a method for identifying an analyte that modulates activity of an agmTA1 receptor, which comprises providing a recombinant cell which produces the agmTA1 receptor; incubating the recombinant cell in a medium with the analyte; and determining the activity of the agmTA1 receptor wherein a change in the activity of the agmTA1 receptor indicates the analyte modulates activity of the agmTA1 receptor.

The activity of the agmTA1 receptor is determined by one or more means for measuring GPCR or TA1 receptor activity selected from the group consisting of measuring a change in the intracellular concentration of $Ca^{2+}$ in the presence of the analyte; measuring a change in the activity of protein kinase A (PKA) in the presence of the analyte; and measuring a change in the synthesis of cyclic AMP (cAMP) in the presence of the analyte. In assays that measure the change in the synthesis of the cAMP, $Ca^{2+}$, or other signaling molecules, an embodiment is further provided wherein measuring the change in signaling molecule is accomplished by including in the recombinant cell a gene expression cassette comprising a reporter gene which encodes an assayable product (e.g., a reporter gene encoding luciferase, β-lactamase, secreted alkaline phosphatase (SEAP), or the like) operably linked to a promoter which is responsive to the signaling molecule.

In a further embodiment of the method, the agmTA1 receptor comprises the amino acid sequence of SEQ ID NO:2. In a further still embodiment of the method, the agmTA1 receptor and/or the chimeric or promiscuous G protein are encoded by gene expression cassettes, which in particular aspects, are integrated into the genome of the recombinant cell. Therefore, the recombinant cell can be transiently or stably transfected with one or more gene cassettes selected from the group consisting of gene cassettes encoding the agmTA1 receptor, a chimeric or promiscuous G protein, and a reporter gene expression cassette.

The present invention further provides a method for identifying an analyte that binds to an agmTA1 receptor, which comprises providing a recombinant cell which produces the agmTA1 receptor; incubating the recombinant cell in a medium with the analyte; and, determining the amount of the analyte bound to the recombinant cell. Analytes which have been identified to bind to the agmTA1 receptor using the aforementioned assays can be further analyzed using one of the functional assays above to determine whether the analyte is an agonist or an antagonist.

In a further embodiment of the method, the agmTA1 receptor comprises the amino acid sequence of SEQ ID NO:2. In a further still aspect of the method, the agmTA1 receptor is encoded by a nucleic acid which in particular embodiments is integrated into the genome of the recombinant cell. In a further embodiment of the above method, a competition assay is provided wherein the recombinant cell is incubated in a medium comprising the analyte and labeled ligand (for example, a ligand selected from the group consisting of tyramine, β-phenylethylamine (β-PEA), tryptamine, and octopamine) and the amount of analyte bound to the agmTA1 receptor on the surface of the recombinant cell is determined by measuring the amount of labeled ligand bound to the recombinant cell. A decrease in the amount of label ligand bound to the recombinant cell indicates that the analyte is a competitor of the labeled ligand for binding to the agmTA1 receptor. In a further still embodiment, the analyte is labeled and the amount of analyte bound to the recombinant cell is determined either alone or in competition with differing concentrations of unlabeled ligand.

The present invention further provides a method for determining whether an analyte is an agmTA1 receptor agonist or antagonist, which comprises providing a membrane which has the agmTA1 receptor integrated therein and a G protein heterotrimer associated therewith; incubating the membrane in the presence of the analyte and labeled GTP for a time sufficient for the labeled GTP to be associated with the membrane when an agonist is present; and separating the membrane from unbound labeled GTP and determining the amount of labeled GTP associated with the membrane wherein an increase in the labeled GTP associated with the membrane indicates that the analyte is an agonist, a decrease in the labeled GTP associated with the membrane indicates that the analyte is an inverse agonist, and a decrease in the labeled GTP associated with the membrane in the presence of ligand (for example, a ligand selected from the group consisting of tyramine, β-phenylethylamine (β-PEA), tryptamine, and octopamine) or known agonist indicates that the analyte is an antagonist.

In a further embodiment of the method, the agmTA1 receptor comprises the amino acid sequence of SEQ ID NO:2. In a further still aspect of the method, the membrane is provided by a recombinant cell comprising a nucleic acid encoding the agmTA1 receptor. In a further still embodiment of the method, the medium comprises the analyte and a labeled ligand. In further still embodiment, the labeled GTP is labeled GTPγS. In particular aspects of the above, the analyte is labeled.

As used throughout the specification and in the appended claims, the singular forms "a," "an," and "the" include the plural reference unless the context clearly dictates otherwise.

As used throughout the specification and appended claims, the following definitions and abbreviations apply.

The term "agmTA1 receptor" means that the TA1 receptor is of *Cercopithecus aethips* (African green monkey) origin, either isolated from African green monkey tissue, produced from a nucleic acid obtained from the monkey by recombinant means, produced from a nucleic acid synthesized in vitro but which encodes the agmTA1 receptor, or synthesized in vitro. The term further includes biologically active fragments or portions of the agmTA1 receptor, including fusion or chimeric proteins.

The term "TA1 receptor" means that the TA1 receptor is not of African green monkey origin. The TA1 receptor can be from another organism, for example, a mammal such as rat and mouse, or a human. The TA1 receptor can either be isolated from tissue of the organism, produced from a nucleic acid obtained from the organism by recombinant means, produced from a nucleic acid synthesized in vitro but which encodes the TA1 receptor, or synthesized in vitro. The term further includes biologically active fragments or portions of the TA1 receptor, including fusion or chimeric proteins.

The term "promoter" refers to a transcription initiation region comprising a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

The term "cassette" or "expression cassette" refers to a nucleotide or gene sequence that is to be expressed from a vector, for example, the nucleotide or gene sequence encoding the agmTA1. In general, a cassette comprises a gene sequence inserted into a vector which in some embodiments provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector include, but are not limited to, enhancers, transcription termination sequences, splice acceptor and donor sequences, introns, ribosome binding sequences, and poly(A) addition sequences.

The term "vector" refers to some means by which DNA fragments can be introduced into a host organism or host tissue. There are various types of vectors including plasmids, viruses (including adenovirus), bacteriophages and cosmids.

"Substantially free from other nucleic acids" means at least 90%, preferably 95%, more preferably 99%, and even more preferably 99.9%, free of other nucleic acids. As used interchangeably, the terms "substantially free from other nucleic acids," "substantially purified," "isolated nucleic acid" or "purified nucleic acid" also refer to DNA molecules which comprise a coding region for an agmTA1 that has been purified away from other cellular components. Thus, an agmTA1 DNA preparation that is substantially free from other nucleic acids will contain, as a percent of its total nucleic acid, no more than 10%, preferably no more than 5%, more preferably no more than 1%, and even more preferably no more than 0.1%, of non-agmTA1 nucleic acids. Whether a given agmTA1 DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

"Substantially free from other proteins" or "substantially purified" means at least 90%, preferably 95%, more preferably 99%, and even more preferably 99.9%, free of other proteins. Thus, an agmTA1 protein preparation that is substantially free from other proteins will contain, as a percent of its total protein, no more than 10%, preferably no more than 5%, more preferably no more than 1%, and even more preferably no more than 0.1%, of agmTA1 proteins. Whether a given agmTA1 protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting.

As used interchangeably, the terms "substantially free from other proteins" or "substantially purified," or "isolated agmTA1" or "purified agmTA1" also refer to agmTA1 that has been isolated from a natural source. Use of the term "isolated" or "purified" indicates that agmTA1 has been removed from its normal cellular environment. Thus, an isolated agmTA1 may be in a cell-free solution or placed in a different cellular environment from that in which it occurs naturally. The term isolated does not imply that an isolated agmTA1 is the only protein present, but instead means that an isolated agmTA1 is substantially free of other proteins and non-amino acid material (e.g., nucleic acids, lipids, carbohydrates) naturally associated with the agmTA1 in vivo. Thus, an agmTA1 protein that is recombinantly expressed in a prokaryotic or eukaryotic cell and substantially purified from this host cell which does not naturally (i.e., without intervention) express this agmTA1 is of course "isolated agmTA1" under any circumstances referred to herein.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term "mammalian" refers to any mammal, including a human being.

The abbreviation "ORF" refers to the open reading frame of a gene.

The term "treatment" refers to both therapeutic treatment and prophylactic or preventative measures. Those in need of treatment include those already with the disorder as well as those prone to have the disorder or those in which the disorder is to be prevented.

A "disorder" is any condition, disease, or the like that would benefit from treatment with analytes identified by the methods described herein. This includes chronic and acute disorders or diseases including those pathological conditions which predispose the mammal to the disorder in question. Examples of disorders that may benefit from treatment with analytes identified by the methods disclosed herein include psychiatric disorders and neurological disorders.

The term "analyte" includes molecule, compound, composition, drug, protein, peptide, nucleic acid, antibody and active fragment thereof, nucleic acid aptamer, peptide aptamer, and the like.

BRIEF DESCRIPTION OF THE DRAWINGS

FIG. 1 shows the nucleic acid sequence (SEQ ID NO:1) encoding the African green monkey trace amine receptor 1.

FIG. 2 shows the amino acid sequence (SEQ ID NO:2) of the African green monkey trace amine receptor 1.

FIG. 3 shows an alignment of the African green monkey trace amine receptor 1 amino acid sequence (SEQ ID NO:2) with the amino acid sequence for the Rhesus monkey trace amine receptor 1 (SEQ ID NO:3), human trace amine receptor 1 (SEQ ID NO: 4), and rat trace amine receptor 1 (SEQ ID NO:5).

DETAILED DESCRIPTION OF THE INVENTION

Figure 4:
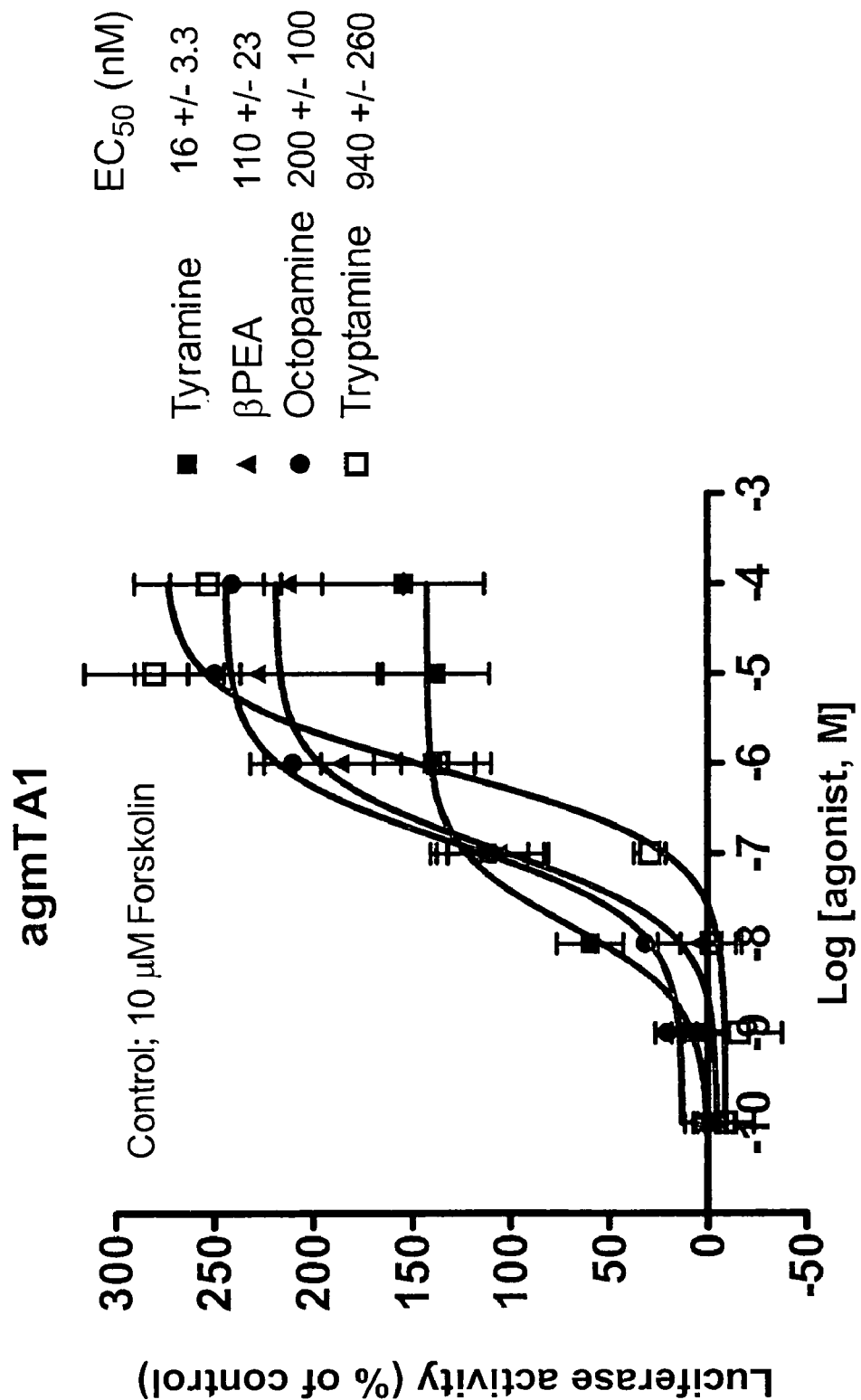
FIG. 4 is a graph showing the $EC_{50}$ for the trace amines tyramine, tryptamine, octopamine, or β-phenylethylamine (βPEA).

The present invention provides nucleic acid molecules that encode the *Cercopithecus aethiops* (African green monkey) trace amine receptor 1 (agmTA1 receptor) and provides methods for using the nucleic acid molecules and the agmTA1 receptor produced therefrom in assays for identifying analytes (molecules, compounds, drugs, or compositions) that modulate the activity of the agmTA1 receptor by interacting with or binding the agmTA1 receptor or modulating the molecular or functional interaction between the agmTA1 receptor and its trace amine ligand (for example, tyramine, tryptamine, octopamine, and β-phenylethylamine). Modulators of agmTA1 receptor activity can be agonists, inverse agonists, or antagonists. Because trace amines can exert pronounced pharmacological effects, the present invention disclosed herein may useful for identifying analytes that inhibit the pharmacological effects. For example, analytes identified using the present invention may be useful for treating a variety of human psychiatric and neurological diseases and disorders. For example, the analytes may be useful for treating depression, psychosis, attention deficit disorder, schizophrenia, Parkinson's disease, substance abuse, eating disorders, epilepsy, or headaches (including primary headaches and migraines).

Non-limiting examples of methods for identifying such analytes include (i) cell-based binding methods for identifying analytes which bind the agmTA1 receptor, inhibit or suppress binding between agmTA1 receptor and its ligand, or interfere with the functional activation of Gα proteins via the agmTA1 receptor in eukaryote cells and (ii) cell-free binding methods for identifying analytes which bind the agmTA1 receptor, inhibit or suppress binding between the agmTA1 receptor and its ligand, or interfere with the functional activation of Gα proteins via the agmTA1 receptor. Thus, the present invention provides a means for identifying agonists and antagonists of the agmTA1 receptor. The methods described herein are useful tools for identifying analytes which modulate molecular and/or functional interactions between the agmTA1 receptor and its ligand or Gα proteins and, therefore, are modulators of the trace amine-dependent signaling pathway.

The present invention is particularly useful for identifying analytes of pharmaceutical importance which can be used to design or develop therapies or treatments for diseases or disorders which involve modulation of agmTA1 receptor activity. Therefore, in one aspect of the present invention, an isolated nucleic acid molecule is provided which comprises a sequence of nucleotides encoding an RNA molecule that can be translated in vivo or in vitro to produce the agmTA1 receptor with the amino acid sequence as set forth in SEQ ID NO:2 (FIG. 2). In further embodiments, the nucleic acid is substantially free from other nucleic acids of the monkey or substantially free from other nucleic acids. In a further embodiment, the isolated nucleic acid molecule comprises the nucleotide sequence set forth in SEQ ID NO:1 (FIG. 1).

The isolated nucleic acid molecules include both deoxyribonucleic acid (DNA) and ribonucleic acid (RNA) molecules encoding the agmTA1 receptor. The isolated nucleic acid molecules further include genomic DNA and complementary DNA (cDNA) encoding the agmTA1 receptor, either of which can be single- or double-stranded, as well as synthetic DNA, such as a synthesized, single stranded polynucleotide. When single-stranded, the DNA molecule can comprise either the coding (sense) strand or the non-coding (antisense) strand. For most cloning purposes, DNA is a preferred nucleic acid.

In further aspects of the present invention, modified agmTA1 receptors are provided which have an amino acid sequence which is substantially similar to the amino acid sequence set forth in SEQ ID NO:2 and nucleic acids which encode the agmTA1 receptor for use in the analyte screening assays disclosed herein. Further provided are nucleic acids encoding the agmTA1 receptor which have a nucleotide sequence substantially similar to the nucleotide sequence set forth in SEQ ID NO:1. As used herein, the term "substantially similar" with respect to SEQ ID NO:2 means that the agmTA1 receptor contains mutations such as amino acid substitution or deletion mutations that do not abrogate the ability of the agmTA1 receptor to bind its ligand. The mutations include naturally occurring allelic variants and variants produced by recombinant DNA methods. As used herein, the term "substantially similar" with respect to SEQ ID NO:1 means that the agmTA1 receptor encoded by the nucleic acid contains mutations such as nucleotide substitution or deletion mutations which do not abrogate the ability of the agmTA1 receptor to bind its ligand. The mutations include naturally occurring allelic variants and variants produced by recombinant DNA methods. In general, any of the foregoing mutations which do not abrogate the ability of the agmTA1 receptor to bind its ligand are conservative mutations.

The present invention further includes biologically active mutants of SEQ ID NO:1. In general, any such biologically active mutant will encode either a polypeptide, which has properties or activity substantially similar to the properties or activity of the agmTA1 receptor, including but not limited to the agmTA1 receptor as set forth in SEQ ID NO:2. Any such polynucleotide includes, but is not limited to, nucleotide substitutions, deletions, additions, amino-terminal truncations, and carboxy-terminal truncations which do not substantially abrogate the properties or activities of the agmTA1 receptor produced therefrom. Thus, the mutations of the present invention encode mRNA molecules that express an agmTA1 receptor in a eukaryotic cell which has sufficient activity (ability to bind one or more of its receptors) to be useful in drug discovery. Further, the present invention provides biologically active fragments of SEQ ID NO:2 and mutants thereof and the DNA encoding such fragments. The biologically active fragments can include any combination of the ligand binding domain, transmembrane domain, and G protein binding domain. For example, the biologically active fragment can consist of the ligand binding domain and the transmembrane domain.

The present invention further includes synthetic DNAs (sDNA) which encode the agmTA1 receptor wherein the nucleotide sequence of the sDNA differs from the nucleotide sequence of SEQ ID NO:1 but still encodes agmTA1 receptor as set forth in SEQ ID NO:2 or mutant with substantially similar properties or activity. For example, to express or enhance expression of the agmTA1 receptor in a particular cell type, it may be necessary to change the sequence comprising one or more of the codons encoding the agmTA1 receptor to sequences to enable expression of the agmTA1 receptor in the particular cell type. Such changes include modifications for codon usage peculiar to a particular host or removing cryptic cleavage or regulatory sites which would interfere with expression of the agmTA1 receptor in a particular cell type. Therefore, the present invention discloses codon redundancies which may result in numerous DNA molecules expressing an identical protein. For purposes of this specification, a sequence bearing one or more replaced codons will be defined as a degenerate variation. Also included within the scope of this invention are mutations either in the DNA sequence or the translated protein that do not alter or do not substantially alter the ultimate physical or functional properties of the expressed protein (in general, these mutations are referred to as conservative mutations). For example, substitution of valine for leucine, arginine for lysine, or asparagine for glutamine may not cause a change in the functionality of the polypeptide.

Included in the present invention are DNA sequences that hybridize to SEQ ID NO:1 under stringent conditions. By way of example, and not limitation, a procedure using conditions of high stringency is as follows. Prehybridization of filters containing DNA is carried out for about 2 hours to overnight at about 65° C. in buffer composed of 6× SSC, 5× Denhardt's solution, and 100 μg/mL denatured salmon sperm DNA. Filters are hybridized for about 12 to 48 hrs at 65° C. in prehybridization mixture containing 100 μg/mL denatured salmon sperm DNA and labeled DNA (for example, 5-20×$10^6$ cpm of $^{32}$P-labeled DNA). The filters are washed at 37° C. for about 1 hour in a solution containing 2× SSC, 0.1% SDS. This is followed by a wash in 0.1× SSC, 0.1% SDS at 50° C. for 45 minutes before autoradiography. Other procedures using conditions of high stringency would include either a hybridization step carried out in 5× SSC, 5× Denhardt's solution, 50% formamide at about 42° C. for about 12 to 48 hours or a washing step carried out in 0.2× SSPE, 0.2% SDS at about 65° C. for about 30 to 60 minutes. Reagents mentioned in the foregoing procedures for carrying out high stringency hybridization are well known in the art. Details of the composition of these reagents can be found in Sambrook et al., Molecular Cloning: A Laboratory Manual $2^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). In addition to the foregoing, other conditions of high stringency which may be used are also well known in the art.

In an another aspect of the present invention, a substantially purified form of an agmTA1 receptor which comprises a sequence of amino acids as disclosed in FIG. 2 (SEQ ID NO:2) is provided. Further provided are biologically active fragments and/or mutants of the agmTA1 receptor, which comprise at least a portion of the amino acid sequence set forth in SEQ ID NO: 2. These mutations or fragments include, but not limited to, amino acid substitutions, deletions, additions, amino terminal truncations, and carboxy-terminal truncations such that these mutations provide for proteins or protein fragments of diagnostic, therapeutic, or prophylactic use and are useful for screening assays for identifying analytes that interfere with the interaction of the agmTA1 receptor and its ligand, such analytes being useful for treatment of diseases or disorders which involve modulation of agmTA1 receptor activity. In a particular embodiment, the present invention provides an isolated nucleic acid molecule comprising a sequence that encodes a mutated agmTA1 receptor comprising the sequence set forth in SEQ ID NO:2 with about 1 to 10 amino acid additions, deletions, or substitutions, wherein the mutated agmTA1 receptor polypeptide is capable of binding its ligand.

The agmTA1 receptors of the present invention can be the "mature" protein or a fragment or portion thereof (e.g., ligand binding domain, transmembrane domain, or G protein binding domain), any of which can be a part of a larger protein such as a fusion protein. It is often advantageous to include covalently linked to the amino acid sequence of the agmTA1 receptor, an additional amino acid sequence which contains secretory or leader sequences, pro-sequences, sequences which aid in purification of the agmTA1 receptors such as multiple histidine residues (polyHis) or antibody-binding epitopes, or one or more additional amino acid sequences which confer stability to the agmTA1 receptor during recombinant production. Thus, agmTA1 receptor fusion proteins are provided which comprise all or part of the agmTA1 receptor linked at its amino or carboxyl terminus to proteins or polypeptides such as green fluorescent protein (GFP), c-myc epitope, alkaline phosphatase, protein A or G, glutathione S-transferase (GST), polyHis, peptide cleavage site, or antibody Fc region. Any such fusion construct can be expressed in a cell line of interest and used to screen for modulators of the agmTA1 receptor disclosed herein. In a particular embodiment, the present invention provides an isolated nucleic acid molecule comprising a sequence that encodes a fusion agmTA1 receptor comprising the sequence set forth in SEQ ID NO:2 or a fusion protein with amino acid additions, deletions, or substitutions, wherein the mutated agmTA1 receptor is capable of binding its ligand.

The present invention further provides vectors which comprise at least one of the nucleic acid molecules disclosed throughout this specification, preferably wherein the nucleic acid molecule is operably linked to a heterologous promoter. These vectors can comprise DNA or RNA. For most cloning purposes, DNA plasmid or viral expression vectors are preferred. Typical expression vectors include plasmids, modified viruses, bacteriophage, cosmids, yeast artificial chromosomes, and other forms of episomal or integrated DNA, any of which expresses the agmTA1 receptor, polypeptide fragment thereof, or fusion protein comprising all or part of the agmTA1 receptor encoded therein. It is well within the purview of the skilled artisan to determine an appropriate vector for a particular gene transfer or other use. As used herein, the term "recombinant agmTA1 receptor" is intended to include any variation of agmTA1 receptor disclosed herein which is expressed from a vector transfected into a eukaryote cell or transformed into a prokaryote cell. Transfected eukaryote cells and transformed prokaryote cells are referred to as recombinant host cells.

An expression vector containing DNA encoding an agmTA1 receptor or any one of the aforementioned variations thereof wherein the DNA is preferably operably linked to a heterologous promoter can be used for expression of the recombinant agmTA1 receptor in a recombinant host cell. Such recombinant host cells can be cultured under suitable conditions to produce recombinant agmTA1 receptor or a biologically equivalent form, for example, as shown in the Examples. Expression vectors include, but are not limited to, cloning vectors, modified cloning vectors, specifically designed plasmids, or specifically designed viruses.

Commercially available mammalian expression vectors which are suitable for recombinant agmTA1 receptor expression include, but are not limited to, pcDNA3.neo (Invitrogen, Carlsbad, Calif.), pcDNA3.1 (Invitrogen, Carlsbad, Calif.), pcDNA3.1/Myc-His (Invitrogen), pCI-neo (Promega, Madison, Wis.), pLITMUS28, pLITMUS29, pLITMUS38 and pLITMUS39 (New England Bioloabs, Beverly, Mass.), pcDNAI, pcDNAIamp (Invitrogen), pcDNA3 (Invitrogen), pMC1neo (Stratagene, La Jolla, Calif.), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Also, a variety of bacterial expression vectors can be used to express recombinant agmTA1 receptor in bacterial cells. Commercially available bacterial expression vectors which may be suitable for recombinant agmTA1 receptor expression include, but are not limited to, pCR2.1 (Invitrogen), pET11a (Novagen, Madison, Wis.), lambda gt11 (Invitrogen), and pKK223-3 (Pharmacia).

In addition, a variety of fungal cell expression vectors may be used to express recombinant agmTA1 receptor in fungal cells. Commercially available fungal cell expression vectors which are suitable for recombinant agmTA1 receptor expression include, but are not limited to, pYES2 (Invitrogen) and *Pichia* expression vector (Invitrogen).

Also, a variety of insect cell expression vectors can be used to express recombinant agmTA1 receptor in insect cells. Commercially available insect cell expression vectors which can be suitable for recombinant expression of agmTA1 receptor include, but are not limited to, pBlueBacIII and pBlueBacHis2 (Invitrogen), and pAcG2T (Pharmingen).

Viral vectors which can be used for expression of recombinant agmTA1 receptor include, but are not limited to, adenovirus vectors, adeno-associated virus vectors, herpesvirus vectors, Sindbis virus vectors, Simliki forest virus vectors, pox virus vectors (such as vaccinia virus, fowl pox, canary pox, and the like), retrovirus vectors, and baculovirus vectors. Many of viral vectors are commercially available.

The nucleic acids of the present invention in the above vectors for expressing the agmTA1 receptor or fragment thereof are preferably assembled into an expression cassette that comprises sequences which provide for efficient expression of the agmTA1 receptor or variant thereof encoded thereon in a eukaryote cell, preferably a mammalian cell such as a CHO cell or variant thereof. The cassette preferably contains the full-length cDNA encoding the agmTA1 receptor or a DNA encoding a fragment of the agmTA1 receptor with homologous or heterologous transcriptional and translational control sequences operably linked to the DNA. Such control sequences include at least a transcription promoter (constitutive or inducible) and transcription termination sequences and can further include other regulatory elements such as transcription enhancers, ribosome binding sequences, splice junction sequences, and the like. In most embodiments, the promoter is a heterologous promoter; however, in particular embodiments, the promoter can be the natural agmTA1 receptor promoter. In either embodiment, the expression cassette allows for ectopic expression of the agmTA1 receptor in various host cells of non-African green monkey origin. In a particularly useful embodiment, the promoter is the constitutive cytomegalovirus immediate early promoter with or without the intron A sequence ($CMV_{ie}$ promoter) although those skilled in the art will recognize that any of a number of other known promoters such as the strong immunoglobulin promoter, Rous sarcoma virus long terminal repeat promoter, SV40 small or large T antigen promoter, or the like. A transcriptional terminator can be the bovine growth hormone terminator although other known transcriptional terminators such as SV40 termination sequences can also be used.

The present invention further provides recombinant host cells transformed or transfected with a vector comprising any one of the aforementioned nucleic acid molecules, particularly host cells transformed or transfected with a vector comprising any one of the aforementioned nucleic acid molecules wherein the nucleic acid molecule is operably linked to a promoter. Recombinant host cells include bacteria such as *E. coli*, fungal cells such as yeast, plant cells, mammalian cells including, but not limited to, cell lines of bovine, porcine, monkey, human, or rodent origin; and insect cells including, but not limited to, *Drosophila* and silkworm-derived cell lines. For instance, one insect expression system utilizes *Spodoptera frugiperda* (Sf21) insect cells (Invitrogen) in tandem with a baculovirus expression vector (pAcG2T, Pharmingen, San Diego, Calif.). Mammalian cells which may be suitable and which are commercially available, include but are not limited to, L cells L-M(TK-) (ATCC CCL-1.3), L cells L-M (ATCC CCL-1.2), Saos-2 cells (ATCC HTB-85), 293 cells (ATCC CRL-1573), Raji cells (ATCC CCL-86), CV-1 cells (ATCC CCL-70), COS-1 cells (ATCC CRL-1650), COS-7 cells (ATCC CRL-1651), CHO-K1 cells (ATCC CCL-61), 3T3 cells (ATCC CCL-92), NIH/3T3 cells (ATCC CRL-1658), HeLa cells (ATCC CCL-2), C127I cells (ATCC CRL-1616), BS-C-1 cells (ATCC CCL-26), MRC-5 cells (ATCC CCL-171), HEK293T cells (ATCC CRL-1573), ST2 cells (Riken Cell bank, Tokyo, Japan RCB0224), C3H10T1/2 cells (JCRB0602, JCRB9080, JCRB0003, or IFO50415), and CPAE cells (ATCC CCL-209). Such recombinant host cells can be cultured under suitable conditions to produce agmTA1 receptor or a biologically equivalent form. Recombinant eukaryote cells include both transiently infected cells and stably transfected cells in which the expression cassette or vector is integrated into the genome of the cell.

As noted above, an expression vector containing DNA encoding agmTA1 receptor or any one of the aforementioned variations thereof can be used to express the agmTA1 receptor encoded therein in a recombinant host cell. Therefore, the present invention provides a process for expressing an agmTA1 receptor or any one of the aforementioned variations thereof in a recombinant host cell comprising introducing the vector comprising a nucleic acid that encodes the agmTA1 receptor into a suitable host cell and culturing the host cell under conditions which allow expression of the agmTA1 receptor and preferably, integration of the agmTA1 receptor into the cell's membrane. In a further embodiment, the agmTA1 receptor has an amino acid sequence substantially as set forth in SEQ ID NO:2 and binds at least its ligand, and the nucleic acid encoding the agmTA1 receptor is operably linked to a heterologous promoter which can be constitutive or inducible. Thus, the present invention further provides a cell comprising a nucleic acid encoding the agmTA1 receptor which has an amino acid sequence substantially as set forth in SEQ ID NO:2, which preferably binds at least its ligand, and wherein the nucleic acid encoding the agmTA1 receptor is operably linked to a heterologous promoter.

Following expression of agmTA1 receptor or any one of the aforementioned variations of the agmTA1 receptor in a host cell, agmTA1 receptor or variant thereof can be recovered to provide agmTA1 receptor in a form capable of binding to its ligand. Several agmTA1 receptor purification procedures are available and suitable for use. The agmTA1 receptor can be purified from cell lysates and extracts by various combinations of, or individual application of, salt fractionation, ion exchange chromatography, size exclusion chromatography, hydroxylapatite adsorption chromatography, or hydrophobic interaction chromatography. In addition, agmTA1 receptor can be separated from other cellular polypeptides by use of an immunoaffinity column made with monoclonal or polyclonal antibodies specific for agmTA1 receptor or a particular epitope thereof. Alternatively, in the case of fusion polypeptides comprising all or a portion of the agmTA1 receptor fused to a second polypeptide, purification can be achieved by affinity chromatography comprising a reagent specific for the second polypeptide such as an antibody or metal.

Cloning, expression vectors, transfections and transformations, and protein isolation of expressed proteins are well known in the art and have been described, for example, in Sambrook et al., Molecular Cloning: A Laboratory Manual $2^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). For example, any of a variety of procedures may be used to clone DNA encoding agmTA1 receptor from RNA isolated from the monkey. These methods include, but are not limited to, the method shown in Examples 1-3 and the following methods.

(1) RACE PCR cloning methods such as disclosed in Frohman et al., Proc. Natl. Acad. Sci. USA 85: 8998-9002 (1988)). 5' and/or 3' RACE can be performed to generate a full-length cDNA sequence. This strategy involves using gene-specific oligonucleotide primers for PCR amplification of agmTA1 receptor cDNA. These gene-specific primers are designed through identification of an expressed sequence tag (EST) nucleotide sequence which has been identified by searching any number of publicly available nucleic acid and protein databases.

(2) Direct functional expression of the agmTA1 receptor cDNA following the construction of an agmTA1 receptor-containing cDNA library in an appropriate expression vector system.

(3) Screening an agmTA1 receptor-containing cDNA library constructed in a bacteriophage or plasmid shuttle vector with a labeled degenerate oligonucleotide probe designed from the amino acid sequence of the agmTA1 receptor.

(4) Screening an agmTA1 receptor-containing cDNA library constructed in a bacteriophage or plasmid shuttle vector with a partial cDNA encoding the agmTA1 receptor. This partial cDNA is obtained by the specific PCR amplification of agmTA1 receptor DNA fragments through the design of degenerate oligonucleotide primers from the amino acid sequence known for other membrane proteins which are related to the agmTA1 receptor.

(5) Screening an agmTA1 receptor-containing cDNA library constructed in a bacteriophage or plasmid shuttle vector with a partial cDNA or oligonucleotide with homology to a mammalian agmTA1 receptor protein. This strategy may also involve using gene-specific oligonucleotide primers for PCR amplification of agmTA1 receptor cDNA identified as an EST as described above.

(6) Designing 5' and 3' gene specific oligonucleotides using SEQ ID NO: 1 as a template so that either the full-length cDNA can be generated by known RACE techniques or a portion of the coding region can be generated by these same known RACE techniques to generate and isolate a portion of the coding region to use as a probe to screen one of numerous types of cDNA and/or genomic libraries in order to isolate a full-length version of the nucleotide sequence encoding agmTA1 receptor.

It would be readily apparent to those skilled in the art that other types of libraries, as well as libraries constructed from other cell types or species types, may be useful for isolating an agmTA1 receptor-encoding DNA or an agmTA1 receptor homologue. Other types of libraries include, but are not limited to, cDNA libraries derived from other cells. The selection of cells or cell lines for use in preparing a cDNA library to isolate a cDNA encoding the agmTA1 receptor can be done by first measuring cell-associated agmTA1 receptor activity using any known assay available for such a purpose.

Preparation of cDNA libraries can be performed by standard techniques well known in the art. Well known cDNA library construction techniques can be found for example, in Sambrook et al., Molecular Cloning: A Laboratory Manual $2^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). Complementary DNA libraries may also be obtained from numerous commercial sources, including but not limited to Clontech Laboratories, Inc. (Palo Alto, Calif.) and Stratagene (La Jolla, Calif.).

The DNA molecules, RNA molecules, and recombinant polypeptides of the present invention can be used to screen and measure levels of agmTA1 receptor expression in homologous or heterologous cells. The recombinant polypeptides, DNA molecules, and RNA molecules lend themselves to the formulation of kits suitable for the detection and typing of agmTA1 receptors. Such a kit would comprise a compartmentalized carrier suitable to hold in close confinement at least one container. The carrier would further comprise reagents such as recombinant agmTA1 receptor or anti-agmTA1 receptor antibodies suitable for detecting agmTA1 receptors. The carrier may also contain a means for detection such as labeled antigen or enzyme substrates or the like. The kit enables identification of polymorphic forms of agmTA1 receptor which can then be used in the previously described methods to determine the effect the polymorphism has on binding between the polymorphic agmTA1 receptor and its ligand.

In accordance with yet another embodiment of the present invention, there are provided antibodies having specific affinity for the agmTA1 receptor or epitope thereof. The term "antibodies" is intended to be a generic term which includes polyclonal antibodies, monoclonal antibodies, Fab fragments, single $V_H$ chain antibodies such as those derived from a library of camel or llama antibodies or camelized antibodies (Nuttall et al., Curr. Pharm. Biotechnol. 1: 253-263 (2000); Muyldermans, J. Biotechnol. 74: 277-302 (2001)), and recombinant antibodies. The term "recombinant antibodies" is intended to be a generic term which includes single polypeptide chains comprising the polypeptide sequence of a whole heavy chain antibody or only the amino terminal variable domain of the single heavy chain antibody ($V_H$ chain polypeptides) and single polypeptide chains comprising the variable light chain domain ($V_L$) linked to the variable heavy chain domain ($V_H$) to provide a single recombinant polypeptide comprising the Fv region of the antibody molecule (scFv polypeptides)(See, Schmiedl et al., J. Immunol. Meth. 242: 101-114 (2000); Schultz et al., Cancer Res. 60: 6663-6669 (2000); Dübel et al., J. Immunol. Meth. 178: 201-209 (1995); and in U.S. Pat. No. 6,207,804 B1 to Huston et al.). Construction of recombinant single $V_H$ chain or scFv polypeptides which are specific against an analyte can be obtained using currently available molecular techniques such as phage display (de Haard et al., J. Biol. Chem. 274: 18218-18230 (1999); Saviranta et al., Bioconjugate 9: 725-735 (1999); de Greeff et al., Infect. Immun. 68: 3949-3955 (2000)) or polypeptide synthesis. In further embodiments, the recombinant antibodies include modifications such as polypeptides having particular amino acid residues or ligands or labels such as horseradish peroxidase, alkaline phosphatase, fluors, and the like. Further still embodiments include fusion polypeptides which comprise the above polypeptides fused to a second polypeptide such as a polypeptide comprising protein A or G.

The antibodies specific for agmTA1 receptor can be produced by methods known in the art. For example, polyclonal and monoclonal antibodies can be produced by methods well known in the art, as described, for example, in Harlow and Lane, Antibodies: A Laboratory Manual. Cold Spring Harbor Laboratory Press: Cold Spring Harbor, N.Y. (1988). The agmTA1 receptor or fragments thereof can be used as immunogens for generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, camelized, CDR-grafted, or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (See, for example, Bahouth et al., Trends Pharmacol. Sci. 12: 338 (1991); Ausubel et al., Current Protocols in Molecular Biology (John Wiley and Sons, N.Y. (1989)).

Antibodies so produced can be used for the immunoaffinity or affinity chromatography purification of the agmTA1 receptor or agmTA1 receptor/ligand complexes. The above referenced anti-agmTA1 receptor antibodies can also be used to modulate the activity of the agmTA1 receptor in living animals, in humans, or in biological tissues isolated therefrom. Accordingly, contemplated herein are compositions comprising a carrier and an amount of an antibody having specificity for agmTA1 receptor effective to block naturally occurring agmTA1 receptor from binding its ligand.

Therefore, the nucleic acids encoding agmTA1 receptor or variant thereof, vectors containing the same, host cells transformed with the nucleic acids or vectors which express the agmTA1 receptor or variants thereof, the agmTA1 receptor and variants thereof, as well as antibodies specific for the agmTA1 receptor, can be used in in vivo or in vitro methods for screening a plurality of analytes to identify analytes that are modulators of the agmTA1 receptor/ligand interaction. These methods provide information regarding the function and activity of the agmTA1 receptor and variants thereof which can lead to the identification and design of molecules, compounds, or compositions capable of specific interactions with African green monkey and ultimately, the human TA1 receptor. In preferred embodiments, the methods identify analytes which interfere with the binding of the agmTA1 receptor to its ligand or activity of the agmTA1 receptor. Such analytes are useful either alone or in combination with other compounds for treating a wide variety of psychiatric or neurological diseases or disorders. Accordingly, the present invention provides methods (screening assays) for identifying analytes that modulate the binding of agmTA1 receptor to its ligand or activity of the agmTA1 receptor and which can be used for treating the aforementioned diseases or disorders. The method involves identifying analytes that bind to the agmTA1 receptor and/or have a stimulatory or inhibitory effect on the biological activity of the agmTA1 receptor or its expression and then determining which of these analytes has an effect on symptoms or diseases regarding the aforementioned disorders and diseases in an in vivo assay.

The screening assays include (i) cell-based methods for identifying analytes which bind the AgmTA1 receptor, inhibit or suppress binding between an agmTA1 receptor and its ligand, or modulate activity of the agmTA1 receptor, and (ii) cell-free methods for identifying analytes which bind the agmTA1 receptor, inhibit or suppress binding between the agmTA1 receptor and its ligand, or modulate activity of the agmTA1 receptor. Analytes that bind or modulate activity of the agmTA1 receptor include both agonists and antagonists. Thomsen et al., Curr. Drug. Discovery, Jan. 13-18 (2004), provide a review of screening assays for identifying modulators of G-protein-coupled receptors, any one of which can be used to identify modulators of the agmTA1 receptor.

Cell-based methods for identifying analytes that bind or modulate the activity of the agmTA1 receptor can be accomplished by any method suitable for measuring the activity of mammalian TA1 receptors, which include for example, many methods suitable for measuring the activity of a G-protein-coupled receptor or any other seven transmembrane receptor. Methods for measuring activity of G-protein coupled receptors (functional assays) include, but are not limited to, measuring alterations in the concentration of intracellular $Ca^{2+}$, inositol triphosphate ($IP_3$), diacylglycerol (DAG), or adenosine cyclic 3',5'-monophosphate (cAMP) in response to an analyte; activation of phospholipase C or protein kinase C (PKC), or alterations in the concentration or activation of other signaling molecules.

Analytes that bind the agmTA1 receptor can be identified in a competitive binding cell-based assay using cells which express the agmTAR1 receptor on the cell surface and labeled-trace amine (for example, tyramine, tryptamine, octopamine, or β-phenylethylamine) as a competitor. In a typical competitive binding assay, eukaryote cells which have been transiently or stably transfected with an expression vector that expresses the agmTA1 receptor are incubated in a cell culture medium suitable for the cells for a time sufficient for the agmTA1 receptor to become integrated into the membranes of the cells. The cells can be adherent cells or non adherent cells. For example, the cells can be adherent cells such as CHO cells which are incubated in cell culture dishes in a medium suitable for growing the CHO cells such that the CHO cells grow in the culture dishes as a monolayer. Alternatively, the cells can be non-adherent cells such as HeLa S cells which are incubated in culture bottles under agitation, e.g., spinner culture bottles. After sufficient time has elapsed to allow a significant number of agmTA1 receptors to be expressed and become integrated into the membranes of the cells, the cells are harvested. In the case of adherent cells, the transfected cells are harvested with an enzyme-free dissociation solution to dislodge the cells from the surface of the tissue culture dishes without causing damage to the agmTA1 receptor integrated into the membranes of the cells. The cells are pelleted by low speed centrifugation and suspended in a buffer. Aliquots of the cells are transferred to buffer containing labeled trace amine and analyte to be tested. After incubating for a time sufficient for trace amine and/or analyte to bind the agmTA1 receptor, unbound labeled trace amine and analyte are removed and the amount of labeled trace amine is then detected by a method suitable for detecting the label. Non-specific binding can be defined as the amount of label bound to the agmTA1 receptor on the cells in the presence of an excess of unlabeled trace amine (e.g., about 200 nM unlabeled trace amine).

In variations of the assay, a plurality of cell aliquots are mixed with aliquots of the mixture containing different concentrations of the analyte to be tested. Analytes which cause a decrease in the amount of label retained relative to controls comprising the labeled trace amine and no analyte are analytes that bind to the agmTA1 receptor. Serial dilutions of the analyte in the presence of a fixed amount of labeled trace amine enable the affinity of the analyte for the agmTA1 receptor to be determined. In an alternative embodiment of the above assay, the trace amine is unlabeled and the analyte is labeled. In this case, analytes which bind the agmTA1 receptor are determined by detecting the amount of labeled analyte bound in the absence and presence of various concentrations of trace amine. In a further alternative of the competitive binding assay, the assay is performed as a cell-free assay wherein membranes comprising the agmTA1 receptor are prepared as described below and incubated with trace amine and analyte as above.

In the assays disclosed herein, determination of the amount of binding in the presence of varying concentrations of analyte and trace amine and analysis of the data by a computer program such as the PRISM software (GraphPad Software, Inc. San Diego, Calif.) can be used to measure the affinity of the analyte for the agmTA1 receptor. Specificity of analytes for the agmTA1 receptor can be determined by measuring the level of labeled trace amine binding in the presence of the analyte to related TAR receptors in similar binding assays using membranes prepared from cells transfected with each respective receptor.

Analytes that can bind to the agmTA1 receptor and which can act as an agonist or antagonist can be determined in a functional or signaling assay. Examples of cell-based functional assays include, but are not limited to, measuring alterations in the concentration of intracellular $Ca^{2+}$ (calcium flux) or adenosine cyclic 3',5'-monophosphate (cAMP) in response to an analyte; or activation of protein kinase A (PKA) in response to an analyte.

Measuring calcium flux in response to an analyte can be used to identify analytes that are G-protein-coupled receptor agonists or antagonists. Binding of a ligand to a G-protein-coupled receptor coupled to Gs activates PKA. The PKA phosphorylates phospholipase C (PLC), which inhibits GPCR-PLC-mediated phosphinositide (PI) generation, and $Ca^{2+}$ release from intracellular $Ca^{2+}$ stores and various receptors such as the $IP_3$ receptor, which reduces its affinity for $IP_3$. This further limits release of the $Ca^{2+}$ from intracellular $Ca^{2+}$ stores. The flux or lack of flux in intracellular $Ca^{2+}$ can be conveniently assessed using fluorescence-based $Ca^{2+}$ release measurements.

Activation of TA1 receptors by trace amines results in an increase in adenylate cyclase activity with a concomitant increase in cAMP levels. The increase in cAMP levels results in an increase in expression of genes regulated by a cAMP-responsive promoter. Agonists and antagonists of the TA1 receptor can be identified in an assay that measures activation of adenylate cyclase via the increase in cAMP. Chen et al., Anal. Biochem. 226: 349-354 (1995), describes a colorimetric assay that uses a recombinant cell transfected with an expression vector encoding a G-protein coupled receptor with a second expression vector containing a promoter with a cAMP responsive element operably linked to the β-galactosidase reporter gene. An alternative assay using enzyme fragment complementation to assay cAMP activity is described in Golla and Seethala, J. Biomol. Screen, 7: 515-525 (2002). Commercially available kits include HITHUNTER cAMP from DiscoveRx Corp. and cAMP DIRECT BIOTRAK kit (Amersham Biosciences). Other methods for measuring changes in cAMP levels are well known in the art.

Therefore, in a further aspect of the present invention, a first gene expression cassette encoding the agmTA1 receptor and a second gene expression cassette encoding a reporter gene encoding an assayable product operably linked to a cAMP responsive promoter, i.e., a promoter comprising one or more cAMP response elements, are transfected into eukaryote cells such as CHO K1 cells. An aliquot of the cotransfected cells is then incubated in a medium containing an analyte, an aliquot containing a known agonist (for example, tyramine, tryptamine, octopamine, or β-phenyl-ethylamine) as a positive control, and an aliquot containing neither the analyte nor the agonist as a negative control. Each of the aliquots further comprises a means for detecting the reporter gene product. An agonist results in an increase in expression of the reporter gene relative to the negative control. To detect an analyte that is an antagonist, aliquots of the cells are incubated in a serial dilution of the analyte in a medium and reporter gene expression measured for each of the aliquots. Then, to each of the aliquots, an agonist is added and reporter gene expression measured. An antagonist results in a decrease in expression of the reporter gene relative to the positive control in the presence of the known agonist.

In a further still aspect, a first gene expression cassette encoding the agmTA1 receptor, a second gene expression cassette encoding a reporter gene encoding an assayable product (e.g., a reporter gene encoding luciferase, β-lactamase, secreted alkaline phosphatase (SEAP), or the like) operably linked to a promoter comprising a cAMP response element, and a third gene expression cassette encoding a chimeric or promiscuous G protein are cotransfected into eukaryote cells. An aliquot of the cotransfected cells are then incubated in a medium containing an analyte, an aliquot with a known agonist as a positive control, and an aliquot with neither the analyte nor the agonist as a negative control. Each of the aliquots further comprises a means for detecting reporter gene expression as described above. To detect an analyte which is an antagonist, aliquots of the cells are incubated in a serial dilution of the analyte in a medium and reporter gene expression measured for each of the aliquots. Then, to each of the aliquots, an agonist is added and reporter gene expression measured.

In an alternative embodiment for measuring the effect on cAMP synthesis, a first gene expression cassette encoding the agmTA1 receptor is transfected into eukaryote cells such as CHO K1 cells. An aliquot of the cotransfected cells is then incubated in a medium containing an analyte, an aliquot with a known agonist (for example, tyramine, tryptamine, octopamine, or β-phenylethylamine) as a positive control, and an aliquot with neither the analyte nor the agonist as a negative control. The levels of cAMP are then measured using any one of a number of commercially available assays for measuring cAMP levels, e.g., the HITHUNTER cAMP kit or the cAMP DIRECT BIOTRAK kit (Amersham Biosciences).

Cell-free assays include contacting agmTA1 receptor (or variant thereof, for example, full-length, a biologically active fragment thereof, or a fusion protein comprising all or a portion of the agmTA1 receptor) with an analyte and determining the ability of the analyte to bind to the agmTA1 receptor or modulate activity of the agmTA1 receptor. Binding of the analyte to the agmTA1 receptor can be determined either directly or indirectly. In one aspect, the assay includes contacting the agmTA1 receptor with a known analyte that binds the agmTA1 receptor to form an assay mixture, contacting the assay mixture with an analyte, and determining the ability of the analyte to interact with the agmTA1 receptor, wherein determining the ability of the analyte to interact with the agmTA1 receptor comprises determining the ability of the analyte to preferentially bind to the agmTA1 receptor as compared to an analyte that is known to bind the agmTA1 receptor, for example, tyramine, tryptamine, octopamine, or β-phenylethylamine. Detection of binding can be direct, for example, wherein the analyte is labeled, or indirectly, for example, in competition assays wherein the analyte competes for binding to the agmTA1 receptor with a trace amine or other analyte known to bind the agmTA1.

The cell-free assays of the present invention can use either a membrane-bound form of agmTA1 receptor or a soluble fragment thereof. In the case of cell-free assays comprising the membrane-bound form of the agmTA1 receptor, it may be desirable to use a solubilizing agent such that the membrane-bound form of the agmTA1 receptor is maintained in solution. Examples of such solubilizing agents include but are not limited to non-ionic detergents such as n-octylglucoside, n-dodecyl glucoside, n-dodecylmaltoside, octanoyl-N-methylglucamide, decanoyl-N-methyl glucamide, Triton X-100, Triton X-114, Thesit, Isotridecypoly(ethylene glycol 5 ether)n, 3-[(3-cholamidopropyl) dimethylamminio]-1-propane sulfonate (CHAPS), 3 [(3-cholamidopropyl) dimethylamminio]-2-hydroxy-1-propane sulfonate (CHAPSO), N-dodecyl=N,N-dimethyl-3-ammonio-1-propanesulfonate.

Analytes that bind the agmTA1 receptor can be identified in a competitive binding cell-free assay using membranes from cells which express the agmTA1 receptor on the cell surface and a labeled-trace amine such as tyramine, tryptamine, octopamine, β-phenylethylamine, or analyte known to bind the agmTA1 receptor as a competitor. In a typical competitive binding assay, eukaryote cells, which have been transiently or stably transfected with an expression vector that expresses the agmTA1 receptor, are incubated in a cell culture medium suitable for the cells for a time sufficient for the agmTA1 receptor to become integrated into the membranes of the cells. The cells can be adherent cells or non adherent cells. For example, the cells can be adherent cells such as CHO cells which are incubated in cell culture dishes in a medium suitable for growing the CHO cells such that the CHO cells grow in the culture dishes as a monolayer. Alternatively, the cells can be non-adherent cells such as HeLa S cells which are incubated in culture bottles under agitation, e.g., spinner culture bottles. After sufficient time has elapsed to allow a significant number of agmTA1 receptors to be expressed and become integrated into the membranes of the cells, the cells are harvested. In the case of adherent cells, the transfected cells are harvested with an enzyme-free dissociation solution to dislodge the cells from the surface of the tissue culture dishes without causing damage to the agmTA1 integrated into the membranes of the cells. The cells are pelleted by low speed centrifugation and suspended in a buffer. Membranes are prepared from the cells and aliquots of the membranes are transferred to buffer containing labeled trace amine such as tyramine, tryptamine, octopamine, β-phenylethylamine, or analyte know to bind the agmTA1 and analyte to be tested. After incubating for a time sufficient for trace amine and/or analyte to bind the agmTA1 receptor, unbound labeled trace amine and analyte are removed and the amount of labeled trace amine is then detected by a method suitable for detecting the label. Non-specific binding can be defined as the amount of label bound to the agmTA1 receptor on the cells in the presence of about 200 nM unlabeled trace amine.

In variations of the assay, a plurality of membrane aliquots are mixed with aliquots of the mixture containing different concentrations of the analyte to be tested. Analytes that cause a decrease in the amount of label retained relative to controls comprising the labeled trace amine or analyte know to bind the agmTA1 and no analyte are analytes that bind to the agmTA1 receptor. Serial dilutions of the analyte in the presence of a fixed amount of labeled trace amine enable the affinity of the analyte for the agmTA1 receptor to be determined. In an alternative embodiment of the above assay, the trace amine is unlabeled and the analyte is labeled. In this case, analytes which bind the agmTA1 receptor are determined by detecting the amount of labeled analyte bound in the absence and presence of various concentrations of trace amine.

A GTP binding assay is an example of a cell-free method which can be used to not only measure binding of an analyte to the agmTA1 receptor but also to determine whether the analyte can modulate activity of the TA1 receptor. Therefore, in a further aspect of a cell-free assay for determining whether an analyte is an agonist or antagonist, a labeled-GTPγS cell-free binding assay method can be used. In this assay, membranes are prepared from transfected cells and aliquots incubated in a mixture with GDP, various concentrations of the analyte, and labeled GTPγS. After incubating for a time sufficient for the labeled GTPγS to bind the G protein, the reaction is terminated and the bound labeled GTPγS is measured by a means suitable for detecting the label. The GTPγS can be labeled by any standard technique known in the art, such as radiolabeling, fluorescence labeling, Europium labeling, or the like. In variations of the assay, a plurality of membrane aliquots are mixed with aliquots of the mixture containing different concentrations of the analyte to be tested. Controls include a trace amine such as tyramine, tryptamine, octopamine, or β-phenylethylamine or analyte known to be an agonist in the absence of the analyte.

When the method is performed in the absence of the trace amine or known agonist, analytes that stimulate labeled GTPγS binding greater than the endogenous level (or non-specific binding level) are agonists while compounds that inhibit the endogenous level of labeled GTPγS are inverse agonists. This is detected as label associated with the membrane. On the other hand, antagonists are detected in a labeled GTPγS binding assay in the presence of a submaximal level of trace amine or other known agonist where they reduce the labeled GTPγS binding that is stimulated by the trace amine. Determination of the amount of binding in the presence of varying concentrations of analyte and analysis of the data by a computer program such as PRISM software (Graphpad) can measure the affinity of analytes for the agmTA1 receptor. Specificity of analytes for the agmTA1 receptor can be determined by measuring the level of labeled GTPγS binding in the presence of the analyte to other G protein coupled receptors (e.g., TAR2, or the like) in similar binding assays using membranes prepared from cells transfected with each respective receptor.

In a further aspect of the method, the analyte is labeled with a label that is different from the label of the GTPγS. For example, the analyte can be labeled with a first fluorescent label which fluoresces at a first wavelength and the GTPγS is labeled with a second fluorescent label which fluoresces at a second wavelength or a radioisotope such as $^{35}S$ or europium. In this embodiment, a labeled analyte, which is an agonist, will bind to the agmTA1 receptor on the membrane and will stimulate binding of the labeled GTPγS to the G protein of the membrane. Both labels will be substantially associated with the membrane and detectable. That is association of both labels with the membrane will be greater than the endogenous level or the non-specific binding level. In contrast, a labeled analyte, which is an antagonist, will bind to the agmTA1 receptor on the membrane but will not stimulate binding of the labeled GTPγS to the G protein of the membrane. The label of the analyte will be substantially associated with the membrane and detectable at a level greater than the endogenous level or the non-specific binding level. However, the labeled GTPγS will not be detectable at a level greater than the endogenous level or the non-specific binding level.

In further aspects of the GTPγS-based method, detection of agonist or antagonist activity of an analyte is determined by determining whether in the presence of the analyte the Gα subunit is activated or rendered inactive. Detection of activated or inactivated Gα subunit can be achieved by including in the assay or subsequent to the assay an antibody or peptide which is specific for and binds either the activated or inactivated form of the Gα subunit. Preferably, the antibody or peptide is labeled.

In various embodiments of the above cell-free assay methods, it may be desirable to immobilize the agmTA1 receptor or a target protein of the agmTA1 receptor to facilitate separation of complexed from uncomplexed forms of one or both, as well as to accommodate automation of the assay. Binding of an analyte to agmTA1 receptor, or interaction of the agmTA1 receptor with a target protein in the presence and absence of an analyte, can be accomplished in any vessel suitable for containing the reactants. Examples of such vessels include microtitre plates, test tubes, microarrays, and microcentrifuge tubes.

In one embodiment, a fusion protein can be provided which adds a domain that allows one or both of the proteins to be bound to a matrix. For example, glutathione-S-transferase (GST) fusion proteins or glutathione-S-transferase fusion proteins can be adsorbed onto glutathione SEPHAROSE beads (Sigma Chemical; St. Louis, Mo.) or glutathione derivatized microtitre plates, which are then combined with the analyte or the analyte and either the non-adsorbed target protein or the agmTA1 receptor, and the mixture incubated under conditions conducive to complex formation (for example, at physiological conditions for salt and pH). Following incubation, the beads or microtitre plate wells are washed to remove any unbound components and complex formation is measured. Alternatively, the complexes can be dissociated from the matrix, and the level of binding or activity of the agmTA1 receptor can be determined using standard techniques. Other techniques for immobilizing proteins on matrices can also be used in the screening assays of the invention. For example, either the agmTA1 receptor or its target trace amine can be immobilized utilizing conjugation of biotin and streptavidin. Biotinylated agmTA1 receptor or target molecules can be prepared from biotin-NHS(N-hydroxy-succinimide) using techniques well known in the art (for example, biotinylation kit, Pierce Chemicals, Rockford, Ill.), and immobilized in the wells of streptavidin coated plates (Pierce Chemical). Alternatively, antibodies reactive with the agmTA1 receptor or target proteins but which do not interfere with binding of the agmTA1 receptor to its target trace amine can be derivatized to the wells of the plate and unbound target or agmTA1 receptor trapped in the wells by antibody conjugation. Methods for detecting such complexes, in addition to those described herein for the GST-immobilized complexes, include immunodetection of complexes using antibodies specific for the agmTA1 receptor or target protein, as well as enzyme-linked assays which rely on detecting an enzymatic activity.

The present invention further provides screening assays for monitoring the expression of the agmTA1 receptor. For example, regulators of expression of the agmTA1 receptor can be identified in a method in which a cell is contacted with an analyte and the expression of agmTA1 receptor (protein or mRNA) in the cell is determined. The level of expression of the agmTA1 receptor in the presence of the analyte is compared to the level of expression of the agmTA1 receptor in the absence of the analyte wherein a change in the level of expression indicates that the analyte can regulate expression of the agmTA1 receptor. For example, an increase in agmTA1 receptor levels in the presence of an analyte indicates that the analyte is a stimulator or inducer of agmTA1 receptor expression. Conversely, an analyte that causes a decrease in agmTA1 receptor levels is an inhibitor of agmTA1 receptor expression. The level of agmTA1 receptor in the cells can be determined by methods well known in the art such as RT-PCR (preferably real-time RT-PCR), Northern blotting, or Western blotting. Preferably, the nucleic acid encoding the agmTA1 receptor is operably linked to its native promoter or an agmTA1 promoter from a non-African green monkey organism.

The method of the present invention can be used for high throughput screening (HTS) of analytes to identify analytes that bind agmTA1 receptor and/or are modulators of agmTA1 receptor activity. Often chemical entities with useful properties are generated by identifying a chemical compound (called a "lead compound") with some desirable property or activity, creating variants of the lead compound, and evaluating the property and activity of those variant compounds. The current trend is to shorten the time scale for all aspects of drug discovery. Because of the ability to test large numbers quickly and efficiently, high throughput screening (HTS) methods are replacing conventional lead compound identification methods.

In one aspect, high throughput screening methods involve providing a library containing a large number of potential agmTA1 receptor modulators (candidate compounds). Such "combinatorial chemical libraries" are then screened in one or more of the assays described herein, to identify those library members particular chemical species or subclasses that display a desired characteristic activity. The compounds thus identified can serve as conventional "lead compounds" or can themselves be used as potential agmTA1 receptor modulators.

Devices for the preparation of combinatorial libraries are commercially available (See, for example, 357 MPS, 390 MPS, Advanced Chem Tech, Louisville, Ky.; Symphony, Rainin, Woburn, Mass.; 433A Applied Biosystems, Foster City, Calif.; 9050 Plus, Millipore, Bedford, Mass.). A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (See, for example, ComGenex, Princeton, N.J.; Asinex, Moscow, Russia; Tripos, Inc., St. Louis, Mo.; ChemStar, Ltd, Moscow, Russia; 3D Pharmaceuticals, Exton, Pa.; Martek Biosciences, Columbia, Md.).

Any of the assays described herein are amenable to high throughput screening. As described above, the agmTA1 receptor modulators are preferably screened by the methods disclosed herein. High throughput systems for such screening are well known to those of skill in the art. Thus, for example, U.S. Pat. No. 5,559,410 discloses high throughput screening methods for protein binding, while U.S. Pat. Nos. 5,576,220 and 5,541,061 disclose high throughput methods of screening for ligand/antibody binding.

In addition, high throughput screening systems are commercially available (See, for example, Zymark Corp., Hopkinton, Mass.; Air Technical Industries, Mentor, Ohio; Beckman Instruments, Inc. Fullerton, Calif.; Precision Systems, Inc., Natick, Mass.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols. Thus, for example, Zymark Corp. provides technical bulletins describing screening systems for detecting the modulation of gene transcription, ligand binding, and the like.

The following examples are intended to promote a further understanding of the present invention.

EXAMPLE 1

The African green monkey trace amine 1 receptor 1 (agmTA1 receptor) was clonsed from the African green monkey genomic DNA library. We reasoned that like the human trace amine receptor 1, the African green monkey ortholog would be a single exon gene. Based on that assumption, we designed PCR primers to the 5' and 3' untranslated regions of the human trace amine receptor 1 gene and used the primers to amplify the gene encoding the African green monkey ortholog from COS-7 genomic DNA.

The complete coding sequence for the agmTA1 receptor was PCR amplified from 200 ng of COS-7 genomic DNA using EXPAND high-fidelity polymerase (Roche Applied Science, Indianapolis, Ind.) with 10 pmole each of the following primers: mTA1F3, 5'-CTGAT TGACA GCCCT CAGG-3' (SEQ ID NO: 6) and mTA1R3, 5'-TGTGG TTGGT GCATG TGG-3' (SEQ ID NO:7). Conditions for PCR were one cycle of 94° C. for 2 minutes; 10 cycles of 94° C. for 30 seconds, 50° C. for 30 seconds, and 68° C. for 1 minute; 25 cycles of 94° C. for 30 seconds, 55° C. for 30 seconds, 68° C. for 1 minute; and, one cycle of 68° C. for 10 minutes. The about 1 kb PCR product was cloned into the plasmid pCR2.1-TOPO (Invitrogen, La Jolla, Calif.) according to the manufacturer's directions. To express the agmTA1 receptor in mammalian cells, the agmTA1 receptor sequence was subcloned as a BamHI/NotI fragment into pcDNA3.1 (+) (Invitrogen) to produce pcDNA3.1-agmTA1. The agmTA1 receptor coding region was verified by sequencing independently amplified PCR products on an ABI 3100 Genetic Analyzer (Applied Biosystems, Foster City, Calif.) using the BIGDYE terminator method.

EXAMPLE 2

This example illustrates a functional assay that can be used to identify analytes that antagonize binding of a trace amine to a trace amine receptor or analytes that activate a trace amine receptor. HEK293 cells were transfected with a vector comprising the agmTA1 receptor operably linked to a constitutive promoter and a vector comprising the luciferase reporter gene operably linked to a promoter containing multiple copies of the cAMP response elements.

The vector comprising the reporter gene was pCRE-Luc (BD Biosciences, Palo Alto, Calif.). The vector comprises the luciferase gene operably linked to a promoter consisting of multiple copies of the CRE-binding sequence fused to a TATA-like promoter (PTAL) region from the herpes simplex virus thymidine kinase (HSV-TK) promoter. The vector enables monitoring of activation of cAMP binding protein (CREB) and cAMP-mediated signal transduction pathways.

A cationic transfection reagent, jetPEI (Qbiogene, Irvine, Calif.) was mixed with pcDNA3.1-agmTA1 and pCRE-Luc in the presence of glycogen. The mixture was put into wells of a collagen I-coated 96-well black/clear bottom plate. The plate was then placed at 4° C. for 12 to 16 hours. The plate with the transfection mixture was then dried in a vacuum centrifuge concentrator (SpeedVac, Savant Instruments, Inc., USA). Next, HEK293 cells were plated into the wells of the dried plate at about 2 to $3 \times 10^5$ cells/well and cultured in Dulbecco's modified Eagles medium (DMEM) containing 10% bovine calf serum for 24 to 27 hours at 37° C. under atmospheric conditions of 94% air-6% $CO_2$.

HEK293 cells transiently expressing the agmTA1 receptor and basal levels of luciferase were washed once with serum- and phenol red-free DMEM and then cultured in DMEM without phenol red in the presence or absence of various concentrations (0.1 nM to 100 μM) of the trace amine ligands (agonists) tyramine, tryptamine, octopamine, or β-phenylethylamine (β-PEA) for 16 to 18 hours at 37° C. under atmospheric conditions of 94% air-6% $CO_2$. A control comprising 10 μM forskolin was included. Afterwards, luciferase activity, which was controlled by activation of the agmTA1 receptor, was determined with a Perkin Elmer LUCLITE kit using TOPCOUNT Microplate Scintillation and Luminescence Counter (Perkin Elmer, Boston, Mass.).

As shown in FIG. 4, effect of the agonists was detectable and quantifiable. As shown, the agonists tyramine and β-PEA were particularly effective, $EC_{50}$ values of about 16 and 110 nM, respectively. The agonists octopamine and tryptamine were less effective, $EC_{50}$ values of about 200 and 940 nM, respectively. The human ortholog has a similar pharmacological profile (See Borowsky et al., Proc. Natl. Acad. Sci. USA 98: 8966-8971 (2001). The above cell-based assay can be adapted to detect antagonists in a competition assay wherein the above reaction is performed using one of the above ligands and various concentrations of the analytes being tested for antagonist activity.

EXAMPLE 3

The following is an example of a cell-free assay that could be used for showing that the agmTA1 receptor ectopically expressed in CHO or HEK293 cells is able to functionally couple GTP to Gα. The functional coupling of the agmTA1 receptor to G proteins can be measured in an $^{35}$S-GTPγS binding assay as follows.

Membranes are prepared from cells transfected with pcDNA3.1-agmTA1 by homogenization in an ice cold buffer such as phosphate buffered saline or 20 mM HEPES pH 7.4, 10 mM EDTA. Homogenates are centrifuged at 48,000×g for 15 minutes at 4° C. and the pellet resuspended in the above buffer and re-centrifuged as above. Following the second centrifugation, the pellet is resuspended in a smaller volume of the same buffer or a buffer such as 20 mM HEPES pH 7.4, 100 mM NaCl, 10 mM MgCl2. The membrane preparation can be frozen at −80° C. until ready for use.

For the assay, aliquots of the membrane preparation are incubated in a volume of about 200 μL of binding buffer per well of a 96 well microtiter dish containing GDP at final concentration of about 5 μM, various concentrations of a trace amine ligand (for example, tyramine, tryptamine, octopamine, or β-phenylethylamine), and $^{35}$S-GTPγS at a final concentration of about 0.1 nM. Binding is performed for about an hour at room temperature and terminated by harvesting the membranes onto GF/B filter plates using a cell harvester filtration device. After drying the filter plates, scintillation fluid is added to each of the wells and bound radioactivity is measured in a scintillation counter.

Coupling of the agmTA1 receptor to G proteins is indicated by detecting $^{35}$S associated with membrane preparations compared to controls without the ligand. By including an analyte in the assay, the assay is a competitive assay which can be used to determine whether the analyte is an antagonist. By substituting the analyte for the ligand, the assay can be used to determine whether the analyte is an agonist.

EXAMPLE 4

A cell-free competition binding assay that could be used for detecting analytes that are competitors of ligand binding to the agmTA1 receptor and determining the analytes' affinity for the agmTA1 receptor can be performed as follows.

HEK293 or CHO cells transfected with pcDNA3.1-agmTA1 are harvested with enzyme-free dissociation solution. Ligand (for example, tyramine, tryptamine, octopamine, or β-phenylethylamine) is labeled. For example, the ligand can be labeled with tritium.

Membranes can be prepared from the transfected cells as in Example 3. Aliquots of the membrane preparation are incubated in about 200 μL binding buffer per well of a 96 well microtiter dish, each well containing a mixture of labeled ligand and unlabeled ligand and an analyte. Binding is performed for about an hour at room temperature and terminated by harvesting the membranes onto GF/B filter plates using a cell harvester filtration device. After drying the filter plates, scintillation fluid is added to each of the wells and bound radioactivity is measured in a scintillation counter. Controls consist of the above assay performed in the absence of the analyte and the above assay performed in the absence of labeled ligand.

Determination of the amount of binding in the presence of varying concentrations of analyte is used to measure the affinity of analytes for the agmTA1 receptor. Specificity of analytes for the agmTA1 receptor is determined by measuring the level labeled ligand binding in the presence of the analyte to related TA1 receptors (for example, trace amine receptors 2 through 15) in similar binding assays using membranes prepared from cells transfected with each respective receptor.

EXAMPLE 5

The following is an example of a method for making polyclonal antibodies that could be used to make polyclonal antibodies specific for the agmTA1 receptor or particular peptide fragments or epitope thereof.

The agmTA1 receptor is produced in E. coli or eukaryote cells transformed with an expression vector comprising DNA encoding the agmTA1 receptor. Antibodies are generated in New Zealand white rabbits over a 10-week period. The agmTA1 receptor or peptide fragment or epitope thereof is emulsified by mixing with an equal volume of Freund's complete adjuvant and injected into three subcutaneous dorsal sites for a total of about 0.1 mg agmTA1 receptor per immunization. A booster containing about 0.1 mg agmTA1 receptor emulsified in an equal volume of Freund's incomplete adjuvant is administered subcutaneously two weeks later. Animals are bled from the articular artery. The blood is allowed to clot and the serum collected by centrifugation. The serum is stored at −20° C.

For purification, the agmTA1 receptor is immobilized on an activated support. Antisera is passed through the sera column and then washed. Specific antibodies are eluted via a pH gradient, collected, and stored in a borate buffer (0.125M total borate) at −0.25 mg/mL. The anti-agmTA1 receptor antibody titers are determined using ELISA methodology with free agmTA1 receptor bound in solid phase (1 pg/well). Detection is obtained using biotinylated anti-rabbit IgG, HRP-SA conjugate, and ABTS.

EXAMPLE 6

The following is a method for making monoclonal antibodies that could be used to make monoclonal antibodies specific for the agmTA1 receptor.

BALB/c mice are immunized with an initial injection of about 1 μg of purified agmTA1 receptor per mouse mixed 1:1 with Freund's complete adjuvant. After two weeks, a booster injection of about 1 μg of the antigen is injected into each mouse intravenously without adjuvant. Three days after the booster injection serum from each of the mice is checked for antibodies specific for the agmTA1 receptor.

The spleens are removed from mice positive for antibodies specific for the agmTA1 receptor and washed three times with serum-free DMEM and placed in a sterile Petri dish containing about 20 mL of DMEM containing 20% fetal bovine serum, 1 mM pyruvate, 100 units penicillin, and 100 units streptomycin. The cells are released by perfusion with a 23 gauge needle. Afterwards, the cells are pelleted by low-speed centrifugation and the cell pellet is resuspended in 5 mL 0.17 M ammonium chloride and placed on ice for several minutes. Then 5 mL of 20% bovine fetal serum is added and the cells pelleted by low-speed centrifugation. The cells are then resuspended in 10 mL DMEM and mixed with mid-log phase myeloma cells in serum-free DMEM to give a ratio of 3:1. The cell mixture is pelleted by low-speed centrifugation, the supernatant fraction removed, and the pellet allowed to stand for 5 minutes. Next, over a period of 1 minute, 1 mL of 50% polyethylene glycol (PEG) in 0.01 M HEPES, pH 8.1, at 37° C. is added. After 1 minute incubation at 37° C., 1 mL of DMEM is added for a period of another 1 minute, then a third addition of DMEM is added for a further period of 1 minute. Finally, 10 mL of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 µM aminopterin, and 10% hybridoma cloning factor (HAT medium). The cells are then plated into 96-well plates.

After 3, 5, and 7 days, half the medium in the plates is removed and replaced with fresh HAT medium. After 11 days, the hybridoma cell supernatant is screened by an ELISA assay. In this assay, 96-well plates are coated with the agmTA1 receptor. One hundred µL of supernatant from each well is added to a corresponding well on a screening plate and incubated for 1 hour at room temperature. After incubation, each well is washed three times with water and 100 µL of a horseradish peroxidase conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 μL of 1 M HCl is added to stop the reaction and the absorbance of the wells is measured at 490 nm. Cultures that have an absorbance greater than the control wells are removed to two $cm^2$ culture dishes, with the addition of normal mouse spleen cells in HAT medium. After a further three days, the cultures are re-screened as above and those that are positive are cloned by limiting dilution. The cells in each two cm2 culture dish are counted and the cell concentration adjusted to $1\times10^5$ cells per mL. The cells are diluted in complete medium and normal mouse spleen cells are added. The cells are plated in 96-well plates for each dilution. After 10 days, the cells are screened for growth. The growth positive wells are screened for antibody production; those testing positive are expanded to 2 $cm^2$ cultures and provided with normal mouse spleen cells. This cloning procedure is repeated until stable antibody producing hybridomas are obtained. The stable hybridomas are progressively expanded to larger culture dishes to provide stocks of the cells.

Production of ascites fluid is performed by injecting intraperitoneally 0.5 mL of pristane into female mice to prime the mice for ascites production. After 10 to 60 days, $4.5\times10^6$ cells are injected intraperitoneally into each mouse and ascites fluid is harvested between 7 and 14 days later.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An isolated African green monkey trace amine receptor 1 (agm TA1 receptor) protein comprising the amino acid sequence set forth in SEQ ID NO:2.

* * * * *

SEQUENCE LISTING

```
<160> NUMBER OF SEQ ID NOS: 7

<210> SEQ ID NO 1
<211> LENGTH: 1017
<212> TYPE: DNA
<213> ORGANISM: Cercopithecus aethiops

<400> SEQUENCE: 1
atgccctttt gccacaatat aattaatact tcctgtgtga aaaacaactg gtcaaatgat     60
gtccgtgctt ccctgtacag tttaatggcg ctcataattc tgaccacatt ggtcggcaat    120
ctgatagtta ttgtttctat atcacacttc aagcaacttc atactccgac aaattggctc    180
attcattcca tggccactgt ggactttctt ctggggtgtc tggtcatgcc ttacagcatg    240
gtgagatctg ctgagcactg ttggtatttt ggagaagtct tctgtaaaat ccacaccagc    300
accgacatta tgctgagctc agcctccatt ttccatctgt ctttcatctc cattgaccgc    360
tactatgctg tgtgtgaccc attgagatat aaagccaaga tcaatatctt ggttatttgt    420
gtgatgatct tcattagttg gagtgtccct gctgtttttg catttgggat gatctttctg    480
gagctaaact tcaaaggcgc tgaagagata tattacaaac atgttcactg cagaggaggt    540
tgctctgtgt tctttagcaa aatatctggg gtactggcct ttatgacttc tttttacata    600
cctggatcta ttatgttatg tatctattac agaatatatc ttatagctaa agagcaggca    660
```

```
agatcaatta atgatgccaa tcagaagctc caaattggat tggaaatgaa aatggaatt    720 tcacaaagca agaaaggaa agctgcgaag acattgggga ttgtgatggg agttttccta    780
atatgctggt gccctttctt tgtctgtaca gtcatcgacc cttttcttca ctacactctt    840
ccacctactt tgaatgatgt attgatttgg tttggctact tgaactctac atttaatcca    900
atggtttatg cattttttcta tccctggttt agaaaagcac tgaagatgat tctgtttggt    960 aaaatttttcc aaaaagattc atccaggtgt aaattatttt tggaatcgag ttcatag    1017
```

<210> SEQ ID NO 2
<211> LENGTH: 338
<212> TYPE: PRT
<213> ORGANISM: Cercopithecus aethiops

<400> SEQUENCE: 2

```
Met Pro Phe Cys His Asn Ile Ile Asn Thr Ser Cys Val Lys Asn Asn
 1               5                  10                  15

Trp Ser Asn Asp Val Arg Ala Ser Leu Tyr Ser Leu Met Ala Leu Ile
            20                  25                  30

Ile Leu Thr Thr Leu Val Gly Asn Leu Ile Val Ile Val Ser Ile Ser
        35                  40                  45

His Phe Lys Gln Leu His Thr Pro Thr Asn Trp Leu Ile His Ser Met
    50                  55                  60

Ala Thr Val Asp Phe Leu Leu Gly Cys Leu Val Met Pro Tyr Ser Met
65                  70                  75                  80

Val Arg Ser Ala Glu His Cys Trp Tyr Phe Gly Glu Val Phe Cys Lys
                85                  90                  95

Ile His Thr Ser Thr Asp Ile Met Leu Ser Ser Ala Ser Ile Phe His
            100                 105                 110

Leu Ser Phe Ile Ser Ile Asp Arg Tyr Tyr Ala Val Cys Asp Pro Leu
        115                 120                 125

Arg Tyr Lys Ala Lys Ile Asn Ile Leu Val Ile Cys Val Met Ile Phe
    130                 135                 140

Ile Ser Trp Ser Val Pro Ala Val Phe Ala Phe Gly Met Ile Phe Leu
145                 150                 155                 160

Glu Leu Asn Phe Lys Gly Ala Glu Glu Ile Tyr Tyr Lys His Val His
                165                 170                 175

Cys Arg Gly Gly Cys Ser Val Phe Phe Ser Lys Ile Ser Gly Val Leu
            180                 185                 190

Ala Phe Met Thr Ser Phe Tyr Ile Pro Gly Ser Ile Met Leu Cys Ile
        195                 200                 205

Tyr Tyr Arg Ile Tyr Leu Ile Ala Lys Glu Gln Ala Arg Ser Ile Asn
    210                 215                 220

Asp Ala Asn Gln Lys Leu Gln Ile Gly Leu Glu Met Lys Asn Gly Ile
225                 230                 235                 240

Ser Gln Ser Lys Glu Arg Lys Ala Ala Lys Thr Leu Gly Ile Val Met
                245                 250                 255

Gly Val Phe Leu Ile Cys Trp Cys Pro Phe Phe Val Cys Thr Val Ile
            260                 265                 270

Asp Pro Phe Leu His Tyr Thr Leu Pro Pro Thr Leu Asn Asp Val Leu
        275                 280                 285

Ile Trp Phe Gly Tyr Leu Asn Ser Thr Phe Asn Pro Met Val Tyr Ala
    290                 295                 300

Phe Phe Tyr Pro Trp Phe Arg Lys Ala Leu Lys Met Ile Leu Phe Gly
305                 310                 315                 320
```

Lys Ile Phe Gln Lys Asp Ser Ser Arg Cys Lys Leu Phe Leu Glu Ser
                325                 330                 335

Ser Ser

<210> SEQ ID NO 3
<211> LENGTH: 338
<212> TYPE: PRT
<213> ORGANISM: Macaca mulatta

<400> SEQUENCE: 3

Met Pro Phe Cys His Asn Ile Ile Asn Ile Ser Cys Val Lys Asn Asn
 1               5                  10                  15

Trp Ser Asn Asp Val Arg Ala Ser Leu Tyr Ser Leu Met Ala Leu Ile
                20                  25                  30

Ile Leu Thr Thr Leu Val Gly Asn Leu Ile Val Ile Val Ser Ile Ser
            35                  40                  45

His Phe Lys Gln Leu His Thr Pro Thr Asn Trp Leu Ile His Ser Met
 50                  55                  60

Ala Thr Val Asp Phe Leu Leu Gly Cys Leu Val Met Pro Tyr Ser Met
65                  70                  75                  80

Val Arg Ser Ala Glu His Cys Trp Tyr Phe Gly Glu Val Phe Cys Lys
                85                  90                  95

Ile His Thr Ser Thr Asp Ile Met Leu Ser Ser Ala Ser Ile Phe His
            100                 105                 110

Leu Ser Phe Ile Ser Ile Asp Arg Tyr Tyr Ala Val Cys Asp Pro Leu
        115                 120                 125

Arg Tyr Lys Ala Lys Ile Asn Ile Leu Val Val Cys Val Met Ile Phe
130                 135                 140

Ile Ser Trp Ser Val Pro Ala Val Phe Ala Phe Gly Met Ile Phe Leu
145                 150                 155                 160

Glu Leu Asn Phe Lys Gly Ala Glu Glu Ile Tyr Tyr Lys His Val His
                165                 170                 175

Cys Arg Gly Gly Cys Ser Val Phe Phe Ser Lys Ile Ser Gly Val Leu
            180                 185                 190

Ala Phe Met Thr Ser Phe Tyr Ile Pro Gly Ser Ile Met Leu Cys Ile
        195                 200                 205

Tyr Tyr Arg Ile Tyr Leu Ile Ala Lys Glu Gln Ala Arg Ser Ile Asn
210                 215                 220

Asp Ala Asn Gln Lys Leu Gln Ile Gly Leu Glu Met Lys Asn Gly Ile
225                 230                 235                 240

Ser Gln Ser Lys Glu Arg Lys Ala Val Lys Thr Leu Gly Ile Val Met
                245                 250                 255

Gly Val Phe Leu Ile Cys Trp Cys Pro Phe Phe Val Cys Thr Val Ile
            260                 265                 270

Asp Pro Phe Leu His Tyr Thr Ile Pro Pro Thr Leu Asn Asp Val Leu
        275                 280                 285

Ile Trp Phe Gly Tyr Leu Asn Ser Thr Phe Asn Pro Met Val Tyr Ala
290                 295                 300

Phe Phe Tyr Pro Trp Phe Arg Lys Ala Leu Lys Met Ile Leu Phe Gly
305                 310                 315                 320

Lys Ile Phe Gln Lys Asp Ser Ser Arg Cys Lys Leu Phe Leu Glu Ser
                325                 330                 335

Ser Ser

<210> SEQ ID NO 4
<211> LENGTH: 339
<212> TYPE: PRT
<213> ORGANISM: Homo Sapiens

<400> SEQUENCE: 4

Met Met Pro Phe Cys His Asn Ile Ile Asn Ile Ser Cys Val Lys Asn
 1               5                  10                  15

Asn Trp Ser Asn Asp Val Arg Ala Ser Leu Tyr Ser Leu Met Val Leu
             20                  25                  30

Ile Ile Leu Thr Thr Leu Val Gly Asn Leu Ile Val Ile Val Ser Ile
         35                  40                  45

Ser His Phe Lys Gln Leu His Thr Pro Thr Asn Trp Leu Ile His Ser
     50                  55                  60

Met Ala Thr Val Asp Phe Leu Leu Gly Cys Leu Val Met Pro Tyr Ser
 65                  70                  75                  80

Met Val Arg Ser Ala Glu His Cys Trp Tyr Phe Gly Glu Val Phe Cys
                 85                  90                  95

Lys Ile His Thr Ser Thr Asp Ile Met Leu Ser Ser Ala Ser Ile Phe
            100                 105                 110

His Leu Ser Phe Ile Ser Ile Asp Arg Tyr Tyr Ala Val Cys Asp Pro
        115                 120                 125

Leu Arg Tyr Lys Ala Lys Met Asn Ile Leu Val Ile Cys Val Met Ile
    130                 135                 140

Phe Ile Ser Trp Ser Val Pro Ala Val Phe Ala Phe Gly Met Ile Phe
145                 150                 155                 160

Leu Glu Leu Asn Phe Lys Gly Ala Glu Glu Ile Tyr Tyr Lys His Val
                165                 170                 175

His Cys Arg Gly Gly Cys Ser Val Phe Phe Ser Lys Ile Ser Gly Val
            180                 185                 190

Leu Thr Phe Met Thr Ser Phe Tyr Ile Pro Gly Ser Ile Met Leu Cys
        195                 200                 205

Val Tyr Tyr Arg Ile Tyr Leu Ile Ala Lys Glu Gln Ala Arg Leu Ile
    210                 215                 220

Ser Asp Ala Asn Gln Lys Leu Gln Ile Gly Leu Glu Met Lys Asn Gly
225                 230                 235                 240

Ile Ser Gln Ser Lys Glu Arg Lys Ala Val Lys Thr Leu Gly Ile Val
                245                 250                 255

Met Gly Val Phe Leu Ile Cys Trp Cys Pro Phe Phe Ile Cys Thr Val
            260                 265                 270

Met Asp Pro Phe Leu His Tyr Ile Ile Pro Pro Thr Leu Asn Asp Val
        275                 280                 285

Leu Ile Trp Phe Gly Tyr Leu Asn Ser Thr Phe Asn Pro Met Val Tyr
    290                 295                 300

Ala Phe Phe Tyr Pro Trp Phe Arg Lys Ala Leu Lys Met Met Leu Phe
305                 310                 315                 320

Gly Lys Ile Phe Gln Lys Asp Ser Ser Arg Cys Lys Leu Phe Leu Glu
                325                 330                 335

Leu Ser Ser

<210> SEQ ID NO 5
<211> LENGTH: 332
<212> TYPE: PRT
<213> ORGANISM: Rattus norvegitus

```
<400> SEQUENCE: 5

Met His Leu Cys His Asn Ser Ala Asn Ile Ser His Thr Asn Ser Asn
 1               5                  10                  15

Trp Ser Arg Asp Val Arg Ala Ser Leu Tyr Ser Leu Ile Ser Leu Ile
             20                  25                  30

Ile Leu Thr Thr Leu Val Gly Asn Leu Ile Val Ile Ile Ser Ile Ser
         35                  40                  45

His Phe Lys Gln Leu His Thr Pro Thr Asn Trp Leu Leu His Ser Met
     50                  55                  60

Ala Val Val Asp Phe Leu Leu Gly Cys Leu Val Met Pro Tyr Ser Met
 65                  70                  75                  80

Val Arg Thr Val Glu His Cys Trp Tyr Phe Gly Glu Leu Phe Cys Lys
             85                  90                  95

Leu His Thr Ser Thr Asp Ile Met Leu Ser Ser Ala Ser Ile Leu His
        100                 105                 110

Leu Ala Phe Ile Ser Ile Asp Arg Tyr Tyr Ala Val Cys Asp Pro Leu
    115                 120                 125

Arg Tyr Lys Ala Lys Ile Asn Leu Ala Ala Ile Phe Val Met Ile Leu
130                 135                 140

Ile Ser Trp Ser Leu Pro Ala Val Phe Ala Phe Gly Met Ile Phe Leu
145                 150                 155                 160

Glu Leu Asn Leu Glu Gly Val Glu Glu Leu Tyr His Asn Gln Val Phe
                165                 170                 175

Cys Leu Arg Gly Cys Phe Pro Phe Phe Ser Lys Val Ser Gly Val Leu
            180                 185                 190

Ala Phe Met Thr Ser Phe Tyr Ile Pro Gly Ser Val Met Leu Phe Val
        195                 200                 205

Tyr Tyr Arg Ile Tyr Phe Ile Ala Lys Gly Gln Ala Arg Ser Ile Asn
    210                 215                 220

Arg Ala Asn Leu Gln Val Gly Leu Glu Gly Glu Ser Arg Ala Pro Gln
225                 230                 235                 240

Ser Lys Glu Thr Lys Ala Ala Lys Thr Leu Gly Ile Met Val Gly Val
                245                 250                 255

Phe Leu Leu Cys Trp Cys Pro Phe Phe Phe Cys Met Val Leu Asp Pro
            260                 265                 270

Phe Leu Gly Tyr Val Ile Pro Pro Thr Leu Asn Asp Thr Leu Asn Trp
        275                 280                 285

Phe Gly Tyr Leu Asn Ser Ala Phe Asn Pro Met Val Tyr Ala Phe Phe
    290                 295                 300

Tyr Pro Trp Phe Arg Arg Ala Leu Lys Met Val Leu Phe Gly Lys Ile
305                 310                 315                 320

Phe Gln Lys Asp Ser Ser Arg Ser Lys Leu Phe Leu
                325                 330

<210> SEQ ID NO 6
<211> LENGTH: 19
<212> TYPE: DNA
<213> ORGANISM: Artificial Sequence
<220> FEATURE:
<223> OTHER INFORMATION: mTA1F3 primer

<400> SEQUENCE: 6
ctgattgaca gccctcagg                                              19

<210> SEQ ID NO 7
```

-continued

```
<211> LENGTH: 18
<212> TYPE: DNA
<213> ORGANISM: Artificial Sequence
<220> FEATURE:
<223> OTHER INFORMATION: mTA1R3 primer

<400> SEQUENCE: 7
tgtggttggt gcatgtgg                                              18
```